United States Patent
Herrmann et al.

(10) Patent No.: US 11,786,570 B2
(45) Date of Patent: Oct. 17, 2023

(54) DERMATOLOGICAL PRODUCT

(71) Applicant: SYMRISE AG, Holzminden (DE)

(72) Inventors: Martina Herrmann, Hameln (DE); Sandra Gaebler, Hoexter (DE); Dominik Stuhlmann, Holzminden (DE); Ann-Christin Weseloh, Polle (DE)

(73) Assignee: SYMRISE AG, Holzminden (DE)

( * ) Notice: Subject to any disclaimer, the term of this patent is extended or adjusted under 35 U.S.C. 154(b) by 18 days.

(21) Appl. No.: 16/976,037

(22) PCT Filed: Feb. 27, 2019

(86) PCT No.: PCT/EP2019/054915
§ 371 (c)(1),
(2) Date: Aug. 26, 2020

(87) PCT Pub. No.: WO2019/166521
PCT Pub. Date: Sep. 6, 2019

(65) Prior Publication Data
US 2021/0290707 A1    Sep. 23, 2021

(30) Foreign Application Priority Data
Feb. 28, 2018 (WO) ................ PCT/EP2018/054986

(51) Int. Cl.
*A61K 36/05* (2006.01)
*A61K 8/9722* (2017.01)
*A61K 8/60* (2006.01)
*A61K 8/67* (2006.01)
*A61K 31/455* (2006.01)
*A61K 47/26* (2006.01)
*A61K 47/40* (2006.01)

(52) U.S. Cl.
CPC ............. *A61K 36/05* (2013.01); *A61K 8/60* (2013.01); *A61K 8/675* (2013.01); *A61K 8/9722* (2017.08); *A61K 31/455* (2013.01); *A61K 47/26* (2013.01); *A61K 47/40* (2013.01)

(58) Field of Classification Search
CPC .................................................. A61Q 19/00
See application file for complete search history.

(56) References Cited

U.S. PATENT DOCUMENTS

2008/0069794 A1* 3/2008 Romanczyk, Jr. ....... A21D 2/36
426/631
2010/0143267 A1 6/2010 Pertile et al.

FOREIGN PATENT DOCUMENTS

| CN | 1819824 A | 8/2006 |
|---|---|---|
| CN | 106334071 A | 1/2017 |
| EP | 2 193 785 A2 | 6/2010 |
| FR | 2980698 A1 | 4/2013 |
| KR | 10-2009-0025431 A | 3/2009 |
| KR | 2011-0044494 A | 4/2011 |
| KR | 2013-0015037 A | 2/2013 |
| KR | 10-2017-0114717 A | 10/2017 |
| WO | WO-2004/047833 A2 | 6/2004 |
| WO | WO-2009/087242 A2 | 7/2009 |

OTHER PUBLICATIONS

Office Action (and English translation) dated Aug. 11, 2021, from counterpart Chinese Application No. 201980016174.8.
Draelos et al., "The effect of 2% niacinamide on facial sebum production," J. Cosmet Laser Ther., 8(2):96-101 (2006).
International Preliminary Report on Patentability for Application No. PCT/EP2018/054986, dated Sep. 1, 2020.
International Preliminary Report on Patentability for Application No. PCT/EP2019/054915, dated Sep. 1, 2020.
International Search Report and Written Opinion for Application No. PCT/EP2018/054986, dated Oct. 30, 2018.
International Search Report and Written Opinion for Application No. PCT/EP2019/054915, dated May 10, 2019.
Tóth et al., "Transient Receptor Potential Vanilloid-1 Signaling as a Regulator of Human Sebocyte Biology," J. Invest. Derm., 129:329-339 (2009).
Walocko et al., "The role of nicotinamide in acne treatment," Dermatol. Ther., 30(5): (2017).
Office Action for Japanese Application No. 2020-545325, dated Dec. 7, 2021.
Decision of Rejection and Withdrawal of Amendment (and English translation) dated Mar. 20, 2023, from counterpart Korean Application No. 10-2020-702800.

* cited by examiner

*Primary Examiner* — Gina C Justice
(74) *Attorney, Agent, or Firm* — MARSHALL, GERSTEIN & BORUN LLP

(57) ABSTRACT

The present invention discloses a composition comprising sugar alcohols or a combination of sugar alcohols and a *Tetraselmis* extract or either of the former together with niacinamide for treating or preventing dysfunctions of the human hair or skin or as a skin or hair care product.

9 Claims, No Drawings

DERMATOLOGICAL PRODUCT

CROSS-REFERENCE TO RELATED APPLICATIONS

This is a U.S. National Phase of International Application No. PCT/EP2019/054915, filed Feb. 27, 2019, which claims priority to International Application No. PCT/EP2018/054986, filed Feb. 28, 2018, the contents of which are incorporated herein by reference.

The present invention discloses a composition comprising a sugar alcohol or a combination of a sugar alcohol and a *Tetraselmis* extract or either of the former together with niacinamide for treating or preventing dysfunctions of the human hair or skin or as a skin or hair care product.

The prior art, US2010143267 A1 (Symrise) describes the use of extracts obtained from *Tetraselmis* sp. amongst others for stimulating the level of cornified envelope protein components such as filaggrin and/or involucrin. Extracts are obtained by extracting viable, freeze-dried or dried cells of *Tetraselmis* sp., preferably *Tetraselmis suecica*, with a liquid extractant selected from the group consisting of hexane, ethyl acetate, ethanol, water, methanol, isopropanol and mixtures of two or more of these extractants for up to 24 h at a temperature of not more than 50° C. According to examples 33 to 40 and 41 to 48, the sequential ethanol extraction at 5 μg/ml is the most effective extraction for increasing involucrin and also filaggrin in ex vivo human skin.

Document EP 2 193 785 A2 is concerned with the extraction of *Tetraselmis suecica*, and discloses compositions comprising a *Tetraselmis suecica* extract. The present composition is different from these compositions in the comprised sugar alcohol.

A composition which combines a *Tetraselmis* extract with high levels of sugar alcohol is not known from the state of the art and has an impact on the skin treatment properties of topical applications employing the inventive composition.

A problem of the present invention was thus to provide new agent compositions suitable for reducing sebum production.

Another problem, to be solved by the present invention, was to obtain new cosmetic or dermatological compositions and products for treating or preventing dysfunctions of the human hair and/or skin and the use of these compositions for cosmetic and therapeutic applications.

The problems relating to the present invention are solved by the following: A composition comprising a sugar alcohol and a *Tetraselmis* extract, wherein the total sugar alcohol content is in an amount of 16 wt. % in the overall composition, calculated based on the extract dry weight and wherein the *Tetraselmis* extract further comprises the following based on the extract dry weight, total minerals 10 wt. % of the total *Tetraselmis* extract composition, further comprises total galactose 3 wt. % of the total *Tetraselmis* extract composition, further comprises total glucose 2 wt. % of the total *Tetraselmis* extract composition, further comprises total amino acids 3 wt. % of the total *Tetraselmis* extract composition and further comprises total nitrogen 2 wt. % of the total *Tetraselmis* extract composition.

The problems of the invention are further solved by a combination composition comprising both sugar alcohol and *Tetraselmis* extract and further comprising niacinamide.

The invention further encompasses a concentrate comprising 0.5 to 80 wt. % of the composition or the combination composition according to the invention, wherein the concentrate comprises 0.5 to 90 wt. % water; 0.5 to 90 wt. % carrier; 0.1 to 5 wt. % of one or more preservatives or preservative system. All weight percentages are calculated based on the *Tetraselmis* extract dry weight.

In particular the invention also encompasses a pharmaceutical or cosmetic product comprising one or more sugar alcohols, preferably mannitol, or a combination of one or more sugar alcohols, preferably mannitol together with niacinamide. These pharmaceutical or cosmetic products are useful in the treatment of skin diseases.

Surprisingly, it was now found that sugar alcohols themselves or sugar alcohols in combination with extracts of the microalgae *Tetraselmis suecica* highly efficiently reduce sebum production.

Furthermore, it was surprisingly found that sugar alcohols themselves or sugar alcohols in combination with *Tetraselmis* extracts potently upregulate many genes involved in epidermal junctions, such as desmosomal ("mechanical"), tight, adherens and gap junctions relevant for cell-to-cell adhesion and tissue integrity as well as allowing of the exchange of ions, second messengers, and small metabolites between adjacent cells.

Furthermore, sugar alcohols themselves or sugar alcohols in combination with *Tetraselmis* extracts surprisingly modulate genes relevant for differentiation and re-epithelialization relevant for processes such as wound healing, tissue regeneration and barrier formation.

Furthermore, we surprisingly discovered that sugar alcohols and of these in particular mannitol, represented by formula (I), itself significantly reduces sebum production.

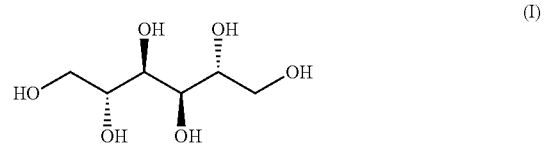 [SMILES: OC[C@@H](O)[C@@H](O)[C@H](O)[C@H](O)CO]

(I)

Mannitol, CAS 69-65-8 (I) is a sugar alcohol. It is an isomer of sorbitol and is typically produced today by the hydrogenation of fructose, which is formed from either starch or sucrose (common table sugar). As a sugar, it is often used as a sweetener in diabetic food, as it is poorly absorbed from the intestines. In cosmetics and beauty products, it is used primarily as a humectant, but can also be found serving as a carrier/diluent, binder, suspending agent, masking agent, moisturizing agent, osmolyte, hydrophilic antioxidant and/or flavoring agent (in lip balms, etc.). Mannitol is also used as a medication e.g. to decrease high pressures in the eyes, seen in glaucoma, and to lower increased intracranial pressure.

Therefore, in a first aspect, the invention relates to a composition comprising a sugar alcohol and a *Tetraselmis* extract, wherein the total sugar alcohol content is in an amount of ≥16 wt. % in the overall composition, calculated based on the extract dry weight and wherein the *Tetraselmis* extract further comprises the following based on the extract dry weight, total minerals 10 wt. % of the total *Tetraselmis* extract composition, further comprises total galactose 3 wt. % of the total *Tetraselmis* extract composition, further comprises total glucose 2 wt. % of the total *Tetraselmis* extract composition, further comprises total amino acids 3 wt. % of the total *Tetraselmis* extract composition and further comprises total nitrogen 2 wt. % of the total *Tetraselmis* extract composition. Preferably, the *Tetraselmis* extract as described herein is a *Tetraselmis suecica* extract.

Tetraselmis biomass can be obtained by cultivation in photobioreactors or in large polyethylene bags or tanks, under daylight or artificial light. The cultivation can occur indoors or outdoors. When the microalgal biomass reaches a suitable cell density, it can be harvested by centrifugation or sedimentation or flocculation or with other techniques suitable to preserve the integrity of the cell material. The harvested biomass is then used fresh (viable) or dried e.g. by freeze- or spray-drying or processed by other suitable technique. As raw material for the extraction, so far unextracted biomass or residual biomass resulting from a prior extraction or processing with organic solvents such as e.g. ethyl acetate, hexane, cyclohexane, acetone, carbon dioxide, methanol, ethanol, propanol, iso-propanol, 1-butanol, 2-butanol, tert-butanol or a mixture of organic solvents can be used.

A method of obtaining the Tetraselmis extract comprises the step of extracting cells of Tetraselmis with a liquid extractant, wherein the extraction comprises: a) exposition of the cell material to the extractant for up to 8 h and b) removal of the cell material to obtain the extract.

The Tetraselmis extract is preferably obtained by extracting cells of Tetraselmis with a liquid extractant. Preferably, the extraction is performed at a temperature higher than 60° C. The Tetraselmis cells are preferably used either fresh (viable), dried, e.g. by freeze- or spray-drying, or processed by other suitable technique.

The liquid extractant suitable for extraction is a polar solvent, i.e. a solvent with a dielectric constant greater than 15. Preferably, the extraction of the Tetraselmis suecica cells is carried out with a polar solvent selected from the group consisting of 2-propanone, ethanol, water, methanol, isopropanol and mixtures of two or more of these solvents.

The ratio of extractant to Tetraselmis matrix is preferably between 80:1 and 3:1. More preferably 20:1 to 8:1. This relatively low ratio with less extractant leads to an improved decoloration effect.

Particularly preferred general extraction processes are maceration, re-maceration, digestion, agitation maceration, vortex extraction, ultrasonic extraction, counter current extraction, percolation, re-percolation, evacolation (extraction under reduced pressure), subcritical or supercritical fluid extraction, diacolation and solid/liquid extraction under continuous reflux. Percolation is even more preferred and was found to have advantageous upscaling properties.

In some preferred case, the extraction is performed twice or three times on the Tetraselmis biomass cell material and the liquid extracts are combined after removing the cell material.

The extraction is carried out by exposing the cell material to the extractant for up to 8 h, preferably at a temperature higher than 60° C. An exposition time of 0.5 to 4 h is preferred. Even more preferred is an exposition time of the cell material to the extractant of 1 to 3 hours.

After extraction of the Tetraselmis cells is completed, the cell material is removed to obtain the extract. Preferably the extract is a dried Tetraselmis extract. In this this case the extracting extractants are removed from the extracted substances.

In the present invention, the Tetraselmis extract is preferably a dried Tetraselmis extract, obtained by removing the extracting extractants, either partially or preferably completely. If the extractants are removed partially, then the remaining extractants are present in the extract in an amount of between 0.5 to 10 wt. %.

Most preferred is that the Tetraselmis extract as described throughout herein is a Tetraselmis suecica extract. Tetraselmis suecica algae have been cultured in Italy for some time, e.g. cultured by an Italian hatchery in Orbetello. Furthermore, six strains of Tetraselmis suecica of different origin are available from CCAP (Culture Collection of Algae and Protozoa), e.g. CCAP 66/4, CCAP 66/22A, CCAP 66/22B, CCAP 66/22C, CCAP 66/22D and CCAP 66/38. However other sources, such as culture collections of Tetraselmis suecica algae can be considered as a potential source of biological material for the present invention.

The resultant extract also does not show an intensive dark green color, but a beige color which is preferred when applying the gained Tetraselmis extract in medical and/or cosmetic and/or other compositions (see operational Example 1).

Additionally, the thus provided Tetraselmis extract is capable of significantly reducing sebum production of the skin (see operational Example 3).

Furthermore, a temperature of more than or equal to 70° C. is preferred for the extraction. This temperature was found to influence the sebum reduction capabilities of the obtained Tetraselmis extract beneficially, but also provided the preferred coloration of the Tetraselmis extract.

Even more preferred is a temperature during exposition of more than or equal to 75° C., most preferred in the range of 75 to 95° C. This temperature not only provides the above-named benefits of coloration and sebum reducing capabilities, but also provides a special Tetraselmis extract which surprisingly influences the gene expression of genes involved in epidermal junctions, antimicrobial peptides, water/glycerol-transport in the skin as well as COX-2 regulation.

In the present application, as indicated above and throughout the application, a Tetraselmis extract is preferably a dried Tetraselmis extract, obtained by removing the extracting extractants, either partially or preferably completely. If the extractants are removed partially, then the remaining extractants are present in the extract in an amount of between 0.5 to 10 wt. %.

In some cases, it is preferred to employ the Tetraselmis extract in its liquid native form, without the drying step. Alternatively, further substances may be added before partial drying, such as glycerin. In such cases, typically an aqueous glycerin solvent system is achieved, with the active components dissolved therein.

Preferably the extract is a dried Tetraselmis suecica extract; in this case the above described method comprises additionally the step c) removing the extracting extractants.

Compositions of Tetraselmis extracts obtained by extraction at 80° C. and at room temperature are specified in Table 2.

The Tetraselmis extract, in particular the Tetraselmis suecica extract, was found to be highly efficient in reducing sebum production. This was particularly effective for extracts comprising mannitol in 10 to 14 wt. %. This is backed by operational Example 3 describing the sebum reducing effect of such an extract. Preferably, the extract comprised total minerals of 15 to 30 wt. %. It is also preferred for the extract to comprise 7 to 20 wt. % total galactose. An amount of galactose within the preferred range hereby increases shelf life of the extract. Furthermore, it is preferred for the extract to contain 5 to 13 wt. % total glucose, which is also increasing shelf life of the extract. Additionally, it is also preferred for the extract to contain at least 6 wt. %, but no more than 16 wt. % total amino acids. Finally, it is preferred for the extract to contain total nitrogen of 3 to 7 wt. % percent of the total composition.

One method to obtain the composition of the present invention is to take the *Tetraselmis* extract matter in the liquid extractant, obtained by extraction according to the method mentioned above, and add sugar alcohol to the *Tetraselmis* extract matter in the liquid extractant in an amount such that the total amount of sugar alcohol in the overall composition is ≥16 wt. %, preferably ≥18 wt. %. Subsequently, it is then preferred that the extracting extractants are removed to obtain a dried product. In some preferred case, the extraction is performed twice or three times on the *Tetraselmis* biomass cell material and the liquid extracts are combined before further addition of the sugar alcohol. Typically, it is preferred that the sugar alcohol added in this way is mannitol.

Another alternative method to obtain the composition of the present invention is to take a dried *Tetraselmis suecica* extract obtained by extraction according to the method mentioned above and add sugar alcohol to the dried *Tetraselmis* extract such that the total amount of sugar alcohol in the overall composition is ≥16 wt. %, preferably ≥18 wt. %. Typically, it is preferred that the sugar alcohol added in this way is mannitol.

Preferably, the *Tetraselmis* extract in the composition of the present invention comprises mannitol of 10 to 14 wt. % and total minerals of 15 to 30 wt. %. It is also preferred for the extract to comprise 7 to 20 wt. % total galactose, more preferably more than 8 wt. % total galactose. An amount of galactose within the preferred range hereby increases shelf-life of the extract. Furthermore, it is preferred for the extract to contain 5 to 13 wt. % total glucose, more preferably more than 4 wt. % total glucose. Additionally, it is also preferred for the extract to contain at least 6 wt. %, but no more than 16 wt. % total amino acids. Finally, it is preferred for the extract to contain total nitrogen of 3 to 7 wt. % percent of the total composition.

Preferably, the *Tetraselmis* extract has a total galactose content, which is the sum of free and bound galactose, of 6 to 12 wt. % of the total composition, even more preferably between 8 to 11 wt. % of the total composition, based on the extract dry weight. This also leads to improved skin hydration properties of cosmetics and medications based on the *Tetraselmis suecica* extract.

Preferably, the *Tetraselmis* extract has a total glucose content, which is the sum of free and bound glucose, of 4 to 10 wt. % of the total composition, even more preferably between 6 to 9 wt. % of the total composition, based on the extract dry weight. This also leads to improved skin hydration properties, especially in cosmetics and medications based on the *Tetraselmis suecica* extract.

Preferably, the *Tetraselmis* extract has a total Arginine content, which is the sum of free and bound Arginine, of 0.1 to 1.5 wt. % of the total composition, even more preferably between 0.6 to 1.0 wt. % of the total composition, based on the extract dry weight.

Preferably, the *Tetraselmis* extract has a total Asparagine content, which is the sum of free and bound Asparagine, of 0.1 to 1.0 wt. % of the total composition, even more preferably between 0.3 to 0.5 wt. % of the total composition, based on the extract dry weight.

Preferably, the *Tetraselmis* extract has a total Aspartic acid content, which is the sum of free and bound Aspartic acid, of less than 0.8 wt. % of the total composition, even more preferably between 0.2 to 0.3 wt. % of the total composition, based on the extract dry weight.

Preferably, the *Tetraselmis* extract has a total Ornithine content, which is the sum of free and bound Ornithine, of less than 1.5 wt. % of the total composition, even more preferably between 0.4 to 0.6 wt. % of the total composition, based on the extract dry weight.

Preferably, the *Tetraselmis* extract is a *Tetraselmis suecica* extract.

A sugar alcohol is the polyalcohol resulting from the reduction of the carbonyl group in a monosaccharide to a hydroxyl group. Sugar alcohols derived from disaccharides are not entirely hydrogenated because only one aldehyde group is available for reduction.

In a preferred first variation of the first aspect, the sugar alcohol is selected from one or more of: C4, C5, C6 or C7 sugar alcohols or disaccharide sugar alcohols.

A *Tetraselmis suecica* extract in synergistically combination with sugar alcohol according to the first variation of the first aspect hereby proves to have an especially pronounced sebum reducing effect.

In a preferred second variation of the first aspect, the sugar alcohol is selected from one or more of: threitol (C4 sugar alcohol), erythritol (C4 sugar alcohol), ribitol (C5 sugar alcohol), arabitol (C5 sugar alcohol), xylitol (C5 sugar alcohol), sorbitol (C6 sugar alcohol), mannitol (C6 sugar alcohol), dulcitol (galactitol) (C6 sugar alcohol), fucitol (C6 sugar alcohol), iditol (C6 sugar alcohol), inositol (cyclic C6 sugar alcohol), volemitol (C7 sugar alcohol), lactiol (4-O-β-D-galactopyranosyl-D-glucitol; C12 disaccharide sugar alcohol), maltitol (4-O-alpha-glucopyranosyl-D-sorbitol; C12 disaccharide sugar alcohol) and their respective enantiomers.

In a more preferred variation of the second variation, the sugar alcohol is selected from one or more of: threitol, erythritol, xylitol, sorbitol, mannitol, inositol, lactiol and maltitol, most preferably the sugar alcohol is mannitol.

The sugar alcohols according to this variation of the first aspect, hereby aside from mannitol, in particular threitol, erythritol, xylitol, sorbitol, inositol, lactiol and maltitol, prove to have a higher sebum reducing effect.

By adding sugar alcohol to the composition of the present invention, the total sugar alcohol content in the composition exceeds the naturally sugar alcohol content of the *Tetraselmis* extract present in the composition.

Consequently, in the thus obtained compositions of the present invention the ratio of the total sugar alcohol content to the sugar alcohol content in the *Tetraselmis* extract based on the extract dry weight is ≥1.1:1, preferably ≥1.3:1 and even more preferred ≥1.5:1.

The *Tetraselmis* extract in synergistic combination with additional sugar alcohols was found to be highly efficient in reducing sebum production. This was particularly effective for compositions comprising a sugar alcohol, preferably mannitol, in more than or equal to 16 wt. % of the total composition, even more preferably more than or equal to 18 wt. % of the total composition and most preferably more than or equal to 25 wt. % of the total composition. This is backed by operational Example 2 describing the sebum reducing effect of such an extract.

Niacinamide, represented by formula (II), also known as nicotinamide, is a water-soluble vitamin in the vitamin B family, specifically the vitamin B3 complex and is found in food, used as a dietary supplement, and cosmetic ingredient in skin and hair care.

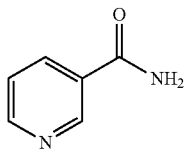

Formula (II)

It is a known sebum reducing (Z. D. Draelos et al., J Cosmet Laser Ther. 2006, 8(2), 96-101), potent anti-inflammatory and anti-acne agent (F. M. Walocko et al., Dermatol Ther. 2017, 30(5). doi: 10.1111/dth.12481). Nicotinamide also improves the epidermal permeability barrier in vivo.

According to the invention, a second aspect of the invention is a combination composition, comprising both a sugar alcohol and a *Tetraselmis* extract according to the invention described herein, further comprising niacinamide. Preferably, the *Tetraselmis* extract as described herein is a *Tetraselmis suecica* extract.

It was not foreseeable that sugar alcohols and *Tetraselmis* extracts in combination with niacinamide exhibit particularly good sebum reducing activity. Surprisingly, it was found by our experimentation that sugar alcohols together with the inventive *Tetraselmis* extract and also niacinamide highly synergistically reduce the total lipids content of sebaceous glands, i.e. sebum level. The enhancing effect of the combination of sugar alcohol and *Tetraselmis* extract on Niacinamide is unexpected.

Particularly effective were combinations in the composition, wherein the weight ratio range of the sugar alcohol and *Tetraselmis* extract to niacinamide is 1:10000 to 1:1, preferably 1:2500 to 1:1, more preferably from 1:500 to 1:10, most preferably 1:400 to 1:300. All combinations are calculated based on the extract dry weight.

Preferred is a sebum reducing composition, consisting of or comprising one or more sugar alcohols and a *Tetraselmis* extract and niacinamide, wherein the sugar alcohol and *Tetraselmis* extract combined are used in an amount of 0.01 to 3 wt. %, preferably 0.1 to 1 wt. %, and niacinamide is used in an amount of for 0.5 to 5 wt. %, preferably 1 to 2 wt. %, based on the total weight of the final (skin care) product and calculated based on the extract dry weight.

It was found that the amounts of sugar alcohol and *Tetraselmis* extract and niacinamide in the formulation adjusted in this way have synergistically enhanced sebum reducing capabilities.

Furthermore, the sugar alcohol and *Tetraselmis* extract (preferably *Tetraselmis suecica*) can be used in the form of a concentrate. Preferably, according to a third aspect of the present invention said concentrate comprises: 0.5 to 80 wt. % of the composition according to the first aspect or the combination composition according to the second aspect, calculated based on extract dry weight, 0.5 to 90 wt. % water, 0.5 to 90 wt. % carrier, and optionally 0.1 to 5 wt. % of one or more preservative or preservative system.

More preferred is a content of 0.5 to 30 wt. % sugar alcohol and *Tetraselmis* extract or combination composition as described above. Furthermore, a content of 10 to 80 wt. % water is more preferably employed. Additionally, a content of 15 to 70 wt. % carrier is preferred.

Preferably, the above concentrate further comprises 0.1 to 5 wt. % of one or more preservative or a preservative system. In another preferred form, the concentrate comprises also stabilizers.

Even more preferred is the use of 0.5 to 2 wt. % of one or more preservatives or preservative systems or stabilizers, as this amount of preservatives or preservative systems or stabilizers was found to positively influence the shelf life of the extract concentrate as described in the third aspect without negatively affecting the positive features, such as sebum-removal-capabilities of the prepared concentrate.

The amount of the respective components is chosen so that it complies with the Cosmetics Directive 76/768/EEC and EU Directive 95/17/EC. Preferably the preservatives are employed according to the classes and compounds listed in the Appendix 6, Parts A and B of the Cosmetics Directive 76/768/EEC. More specific preferable preservatives are benzoic acid, sodium benzoate, sorbic acid, lactic acid, potassium sorbate, phenoxyethanol, or combinations thereof. Lactic acid is preferred. Most preferred is sorbic acid. Preservative boosters are preferably hydroxyacetophenone, 1,2-pentanediol, 1,2-hexanediol, 1,2-octanediol or combinations thereof. However, 1,2-pentanediol may also be used in higher amounts as a secondary liquid carrier.

In the concentrate according to the third aspect of the present invention, comprising the sugar alcohol and *Tetraselmis* extract (preferably *Tetraselmis suecica*), the ratio of the total sugar alcohol content to the sugar alcohol content in the *Tetraselmis* extract based on the extract dry weight is ≥1.1:1, more preferably ≥1.3:1 and still more preferred ≥1.5:1. The sugar alcohol originally from the extract may only be about 11 wt. % based on extract dry weight. However, for the invention, a higher sugar alcohol content in the composition is preferred, with 16 wt. % or more. To achieve this, sugar alcohol is added to the composition. Thereafter, even if the composition is diluted or concentrated in a liquid or solid concentrate, the total sugar alcohol in either composition or concentrate will be higher than if it came only from the extract. The ratio of total sugar alcohol content to the native sugar alcohol from the extract is therefore always greater than 1:1. The above ratio therefore distinguishes between added sugar alcohol and native sugar alcohol from the extract to give a total sugar alcohol content.

More preferably, the above concentrate is either a liquid or solid concentrate. If the concentrate is a liquid concentrate it advantageously comprises 1 to 70 wt. % water, more preferably 30 to 60 wt. % water.

More preferably, the concentrate is a liquid concentrate comprising:
  a) 0.5 to 20 wt. %, preferably 0.5 to 10 wt. %, of the composition or a combination composition according to the invention,
  b) 1 to 70 wt. % water,
  c) 0.5 to 85 wt. % liquid carrier, preferably glycerin, and
  d) optionally 0.1 to 5 wt. % of one or more preservative or preservative system.

The weight ratios are calculated based on *Tetraselmis* extract dry weight.

It is particularly preferred, when the concentrate is a liquid concentrate comprising:
  a) 0.5 to 20 wt. % (preferably 0.5 to 10 wt. %) of the composition or a combination composition according to the present invention,
  b) 40 to 65 wt. % water,
  c) 25 to 55 wt. % glycerin,
  d) 0.1 to 1 wt. % potassium sorbate
  e) 0.1 to 1 wt. % sodium benzoate and
  f) 0.1 to 5 wt. % lactic acid.

The weight ratios are calculated based on *Tetraselmis* extract dry weight.

In the liquid concentrate, comprising the sugar alcohol and *Tetraselmis* extract (preferably *Tetraselmis suecica*), the ratio of the total sugar alcohol content to the sugar alcohol content in the *Tetraselmis* extract based on the extract dry weight is ≥1.1:1, more preferably ≥1.3:1 and still more preferred ≥1.5:1.

Liquid concentrate is preferably produced after extraction and separation of the biomass from the extract solution by partially or complete removal of the extractant and optional addition of a liquid carrier such as e.g. glycerin, propylene glycol, butylene glycol, 1,3-propanediol, 1,2-pentanediol, 1,2-hexanediol, preferably glycerin, or mixtures of two or more of these and optional addition of a preservative or preservative system. Such systems can optionally comprise 0.1 to 5 wt. % of the preservative.

Also preferred is that the concentrate is a solid concentrate comprising:
 a) 1 to 30 wt. % (preferably 1 to 10 wt. %) of the composition or a combination composition according to the invention,
 b) 0.5 to 8 wt. % water, and
 c) 50 to 98 wt. % solid carrier, preferably maltodextrin.
The weight ratios are calculated based on *Tetraselmis* extract dry weight.

In the solid concentrate, comprising the sugar alcohol and *Tetraselmis* extract (preferably *Tetraselmis suecica*), the ratio of the total sugar alcohol content to the sugar alcohol content in the *Tetraselmis* extract based on the extract dry weight is ≥1.1:1, more preferably ≥1.3:1 and still more preferred ≥1.5:1.

In another preferred form, this solid concentrate comprises a preservative or preservative system.

The solid concentrate is gainfully produced after extraction and separation of the biomass from the extract solution either without or with prior partially removal of the extractant and after optional addition of a solid carrier such as e.g. modified starches like maltodextrin, dextrin or cyclodextrin, lactose, modified celluloses, gums like xanthan gum, gellan gum, guar gum, gum arabic, gum ghatti, tragacanth gum or locust bean gum, silicon dioxide, preferably maltodextrin or mixtures of two or more of these by drying using suitable processes such as spray-, freeze- or vacuum drying.

The above liquid or solid concentrates can be employed in cosmetic and/or dermatological and/or pharmaceutical products for skin and hair care and cleansing in an amount of 0.0001 to 10 wt. %, preferably 0.001 to wt. 5% and most preferably 0.005 to 3 wt. % of the final products.

It was found that these liquid or solid concentrates show good storage properties, are easy to handle, dose and formulate.

In a further inventive fourth aspect, particularly preferred is a pharmaceutical composition comprising the composition according to the first aspect or combination composition according to the second aspect, or a concentrate according to the third invention aspect, which is used as a medicament for treating skin related diseases and medical conditions.

In a preferred first variation of the fourth aspect, the sugar alcohol of the pharmaceutical composition is selected from one or more of: threitol (C4 sugar alcohol), erythritol (C4 sugar alcohol), ribitol (C5 sugar alcohol), arabitol (C5 sugar alcohol), xylitol (C5 sugar alcohol), sorbitol (C6 sugar alcohol), mannitol (C6 sugar alcohol), dulcitol (galactitol) (C6 sugar alcohol), fucitol (C6 sugar alcohol), iditol (C6 sugar alcohol) inositol (cyclic C6 sugar alcohol), volemitol (C7 sugar alcohol), lactiol (4-O-β-D-galactopyranosyl-D-glucitol; C12 disaccharide sugar alcohol), maltitol (4-O-alpha-glucopyranosyl-D-sorbitol; C12 disaccharide sugar alcohol) and their respective enantiomers, preferably threitol, erythritol, xylitol, sorbitol, mannitol, inositol, lactiol and maltitol and most preferably mannitol.

In a preferred variation of the fourth aspect, the sugar alcohol in the pharmaceutical composition, preferably mannitol, is in an amount of 0.0001 to 5 wt. %, preferably 0.005 to 3 wt. % in the total pharmaceutical composition.

Especially preferred is a pharmaceutical composition as described herein, which is used as a medicament for treating or preventing dysfunctions of human hair and/or skin, seborrhoeic dermatitis (seborrhea), acne vulgaris, wound healing, tissue regeneration, post-inflammatory hyperpigmentation, inflammatory related diseases, dandruff or *Pityriasis versicolor*. Treatment of *Pityriasis versicolor* is preferably achieved by reducing *Malassezia*.

Hereby, it is more preferred that the pharmaceutical composition as described by the present fourth aspect, is used as a medicament for treating or preventing dysfunctions of human hair and/or skin, inflammatory related diseases, acne and dandruff, wherein it is most preferred for the pharmaceutical composition to be a sugar alcohol or a combination of sugar alcohol and niacinamide according to the previously described aspects.

Interestingly, a pharmaceutical composition, more preferably a composition in accordance with the first inventive aspect of the present invention or a combination composition in accordance with the second inventive aspect of the present invention is especially effective when used as a medicament for preventing of treating dysfunctions of human hair and/or skin, inflammatory related diseases, acne and dandruff.

Furthermore, especially preferred is a combination composition as described by the present invention, which is used as a medicament for treating or preventing dysfunctions of human hair and/or skin, seborrhoeic dermatitis (seborrhea), acne vulgaris, wound healing, tissue regeneration, post-inflammatory hyperpigmentation, inflammatory related diseases, dandruff or *Pityriasis versicolor*. Treatment of *Pityriasis versicolor* is preferably achieved by reducing *Malassezia*.

Even more preferred is the use of the concentrate according to the third aspect of the present invention as a medicament for treating or preventing dysfunctions of human hair and/or skin, acne vulgaris or seborrheic dermatitis, wherein it is most preferred for the *Tetraselmis* extract to be an extract obtained from *Tetraselmis suecica* according to the previously described aspects.

In a fifth aspect, particularly preferred is a pharmaceutical product comprising one or more sugar alcohols, preferably mannitol, or a combination of one or more sugar alcohols and niacinamide.

In a preferred variation of the fifth aspect, the sugar alcohol is selected from one or more of: C4, C5, C6, C7 sugar alcohols and C12 disaccharide sugar alcohols.

In a preferred second variation of the fifth aspect, the sugar alcohol is selected from one or more of: threitol (C4 sugar alcohol), erythritol (C4 sugar alcohol), ribitol (C5 sugar alcohol), arabitol (C5 sugar alcohol), xylitol (C5 sugar alcohol), sorbitol (C6 sugar alcohol), mannitol (C6 sugar alcohol), dulcitol (galactitol) (C6 sugar alcohol), fucitol (C6 sugar alcohol), iditol (C6 sugar alcohol), inositol (cyclic C6 sugar alcohol), volemitol (C7 sugar alcohol), lactiol (4-O-β-D-galactopyranosyl-D-glucitol; C12 disaccharide sugar alcohol), maltitol (4-O-alpha-glucopyranosyl-D-sorbitol; C12 disaccharide sugar alcohol) and their respective enantiomers.

In a more preferred variation of the second variation, the sugar alcohol is selected from one or more of: threitol, erythritol, xylitol, sorbitol, mannitol, inositol, lactiol and maltitol, most preferably the sugar alcohol is mannitol.

The sugar alcohols according to the fifth aspect hereby proves to have an especially pronounced sebum reducing effect (see operational Examples 6 and 7). Furthermore, the sugar alcohols are assumed to increase epidermal skin hydration by their water-holding capacity, despite their sebum reducing effect. Additionally, mannitol not only provides the above-named benefits of sebum reducing capabilities (see operational Example 4), but also surprisingly influences the gene expression of genes involved in epidermal junctions, antimicrobial peptides, water/glycerol-transport in the skin as well as COX-2 regulation (see operational Example 5). Beside the above-named effects, the sugar alcohols according to the fifth aspect improve the shelf-life and compatibility of the composition.

According to the invention, a third variation of the fifth aspect is a combination of one or more sugar alcohols, especially as described above, and niacinamide. This combination with niacinamide has enhanced skin hydration and is particularly suitable for skin moisturizing.

It was not foreseeable that sugar alcohols in combination with niacinamide exhibit particularly effective sebum reducing activity. Surprisingly, it was found by our experimentation that sugar alcohols and niacinamide in combination highly synergistically reduce the total lipids content of sebaceous glands, i.e. sebum level (see operational Example 8). The enhancing effect of the combination of one or more sugar alcohols and niacinamide is unexpected.

Particularly effective were combinations in the composition, wherein the weight ratio range of sugar alcohols, preferably mannitol, to niacinamide is 1:10000 to 1:1, preferably 1:2500 to 1:1, more preferably from 1:500 to 1:10, most preferably 1:400 to 1:300. Alternatively, the weight ratio range in the pharmaceutical composition of the sugar alcohol component in relation to niacinamide is 1:100 to 1:1, preferably 1:50 to 1:1.

It was found that the amounts of sugar alcohol component with one or more sugar alcohols, in particular mannitol, and at the same time niacinamide in the formulation adjusted in this way have synergistically sebum reducing capabilities.

Especially preferred is a pharmaceutical product as described herein, which is used as a medicament for treating or preventing dysfunctions of human hair and/or skin, seborrhoeic dermatitis (seborrhea), acne vulgaris, wound healing, tissue regeneration, post-inflammatory hyperpigmentation, inflammatory related diseases, dandruff or *Pityriasis versicolor*. Treatment of *Pityriasis versicolor* is preferably achieved by reducing *Malassezia*.

Hereby, it is more preferred that the pharmaceutical product as described by the present fifth aspect, is used as a medicament for treating or preventing dysfunctions of human hair and/or skin, inflammatory related diseases, acne and dandruff, wherein it is most preferred for the pharmaceutical product to comprise a sugar alcohol or a combination of sugar alcohols and niacinamide according to the previously described aspects.

Surprisingly, the combination of niacinamide and one or more sugar alcohols as described by the previous inventive aspects, especially when the contained sugar alcohol is one according to the first or second variation of the invention, is especially effective when used as a medicament for treating or preventing dysfunctions of human hair and/or skin, acne vulgaris or seborrheic dermatitis.

In another preferred variation of the fourth or fifth aspect, the amount of the sugar alcohol, preferably mannitol in the pharmaceutical composition or the pharmaceutical product according to the invention or the pharmaceutical product is 0.0001 to 5 wt. %, preferably 0.005 to 3 wt. % in the total pharmaceutical composition or pharmaceutical product.

Preferred is a sebum reducing pharmaceutical product, consisting of or comprising one or more sugar alcohols in combination with niacinamide, wherein the combination of sugar alcohol and niacinamide is used in an amount of 0.5 to 5 wt. %, based on the total weight of the final product.

Additionally, the weight ratio range of niacinamide in the pharmaceutical composition according to the fourth aspect or the weight ratio range in the pharmaceutical product according to the fifth aspect is 0.0001 to 5 wt. %, preferably 0.005 to 3 wt. % in the total pharmaceutical composition or pharmaceutical product which is especially preferred, for the use as a medicament for treating or preventing dysfunctions of human hair and/or skin, seborrhoeic dermatitis (seborrhea), acne vulgaris, wound healing, tissue regeneration, post-inflammatory hyperpigmentation, inflammatory related diseases, dandruff or *Pityriasis versicolor*. Treatment of *Pityriasis versicolor* is preferably achieved by reducing *Malassezia*.

The sugar alcohol as described in previous inventive aspects of the invention is found to be effective when used as a medicament for treating or preventing dysfunctions of the human hair and/or skin, inflammatory related diseases or *acnes*. Hereby, it is highly preferred for the sugar alcohol according to the second variation of the fourth aspect, to be used as a medicament for treating or preventing dysfunctions of the human hair and/or skin, inflammatory related diseases or acne.

Further, the invention describes a dermatological or therapeutic product comprising a pharmaceutical composition or a pharmaceutical product according to the invention and optionally auxiliary substances, for use in treating skin diseases.

The preparations can also contain water in a quantity of up to 99 wt. %, preferably 5 to 80 wt. %, based on the total weight of the preparation. Hereby it is even more preferred for the formulations according to the invention to be a e.g. W/O (water-in-oil) emulsion, O/W (oil-in-water) emulsion, W/O/W (water-in-oil-in-water) emulsion, O/W/O (oil-in-water-in-oil) emulsion.

Auxiliary substances and additives can be included in quantities of 0.1 to 99 wt. %, preferably 1 to 90 wt. %, preferably 60 to 80 wt. %, based on the total weight of the formulation.

It is preferred for the auxiliary substances and/or additives to be chosen from one or more of the groups of cooling agents, film-forming substances, anti-oxidants, vitamins, 2-hydroxycarboxylic acids, skin colouring agents, skin-moisturising substances, fats/fatty acids, waxes or other conventional constituents of a cosmetic or dermatological formulation such as alcohols, polyols, polymers, foam stabilisers, electrolytes, organic solvents, silicone derivatives or chelating agents, perfumes, substances to prevent foaming, dyes, pigments having a colouring action, thickeners, surface-active substances, emulsifiers, plant parts and plant extracts, animal extracts, propolis, proteins, protein hydrolysates and yeast extracts.

Hereby it is especially preferred for the film-forming substance to be chosen from e.g. polyvinyl pyrrolidones or chitosan or derivatives thereof;

for the vitamins to be chosen form e.g. vitamin C and derivatives, tocopherols and derivatives, vitamin A and derivatives;

for the 2-hydroxycarboxylic acids to be chosen form e.g. citric acid, malic acid, L-, D- or di-lactic acid;

for the skin colouring agents to be chosen from e.g. walnut extracts or dihydroxyacetone;

for the skin-moisturizing agents to be chosen form e.g. glycerol or urea;

for the fatty acids to be chosen from either of or combinations of the subgroups of monounsaturated or polyunsaturated fatty acids or α-hydroxy acids or polyhydroxy fatty acids or derivatives thereof such as e.g. linoleic acid, α-linolenic acid, γ-linolenic acid or arachidonic acid and the natural or synthetic esters thereof;

for the chelating agents to be chosen form e.g. ethylene diamine tetraacetic acid and derivatives;

for the thickeners to be chosen form silicon dioxide, aluminium silicates, such as e.g. bentonites, polysaccharides or derivatives thereof, e.g. hyaluric acid, guar gum, xanthan gum, hydroxypropyl methylcellulose or allulose derivatives, particularly advantageously polyacrylates such as e.g. carbopols or polyurethanes;

for the plant parts and plant extracts to be chosen from either or combinations of either of the plants e.g. arnica, aloe, beard lichen, ivy, stinging nettle, ginseng, henna, camomile, marigold, rosemary, sage, horsetail, oat, ginger, hop, wheat or thyme; when said compound group is employed as an auxiliary substance and/or additive.

In a further sixth invention aspect, we present a cosmetic composition comprising a composition or combination composition according to the invention or a cosmetic product comprising one or more sugar alcohols, preferably mannitol, or a combination of one or more sugar alcohols and niacinamide. Particularly preferred is a cosmetic composition comprising a composition or a combination composition or a concentrate or a cosmetic product according to the invention, and optionally auxiliary substances and/or perfumes, wherein the cosmetic composition or cosmetic product is a human skin and/or hair care product.

In a preferred first variation of the sixth aspect, the sugar alcohol is selected from one or more of: C4, C5, C6, C7 sugar alcohols and disaccharide sugar alcohols.

A sugar alcohol according to the first variation of the sixth aspect hereby proves to have an especially pronounced sebum reducing effect.

In a preferred second variation of the sixth aspect, the sugar alcohol is selected from one or more of: threitol (C4 sugar alcohol), erythritol (C4 sugar alcohol), ribitol (C5 sugar alcohol), arabitol (C5 sugar alcohol), xylitol (C5 sugar alcohol), sorbitol (C6 sugar alcohol), mannitol (C6 sugar alcohol), dulcitol (galactitol) (C6 sugar alcohol), fucitol (C6 sugar alcohol), iditol (C6 sugar alcohol), inositol (cyclic C6 sugar alcohol), volemitol (C7 sugar alcohol), lactiol (4-O-β-D-galactopyranosyl-D-glucitol; C12 disaccharide sugar alcohol), maltitol (4-O-alpha-glucopyranosyl-D-sorbitol; C12 disaccharide sugar alcohol) and their respective enantiomers.

In a more preferred variation of the second variation, the sugar alcohol is selected from one or more of: threitol, erythritol, xylitol, sorbitol, mannitol, inositol, lactiol and maltitol, most preferably the sugar alcohol is mannitol.

The sugar alcohol according to the second variation of the sixth aspect has a strong sebum reducing effect.

According to the invention, a third variation of the sixth aspect is a combination of one or more sugar alcohols and niacinamide. This combination with niacinamide has enhanced skin hydration and is particularly suitable for skin moisturizing.

It was not foreseeable that sugar alcohol in combination with niacinamide exhibit particularly good sebum reducing activity. Surprisingly, it was found by our experimentation that sugar alcohols, in particular sorbitol and mannitol, and niacinamide highly synergistically reduce the total lipids content of sebaceous glands, i.e. sebum level (see operational Example 8). The enhancing effect of the combination of sugar alcohol and niacinamide is unexpected.

Particularly effective were combinations in the composition, wherein the weight ratio range of sugar alcohol to niacinamide is 1:10000 to 1:1, preferably 1:2500 to 1:1, more preferably from 1:500 to 1:10, most preferably 1:400 to 1:300. Alternatively, the weight ratio range in the pharmaceutical or cosmetic composition of the sugar alcohol in relation to niacinamide is 1:100 to 1:1, preferably 1:50 to 1:1.

It was found that the amounts of sugar alcohol and niacinamide in the formulation adjusted in this way have synergistically sebum reducing capabilities.

Preferred is a sebum reducing cosmetic product, consisting of or comprising sugar alcohol and niacinamide, wherein the combination of sugar alcohol and niacinamide is used in amount of 0.1 to 5 wt. %, based on the total weight of the final cosmetic (skin care) product.

Further preferred is that the dermatological or therapeutic product as previous mentioned according to the invention, wherein the amount of the composition, the combined composition or the concentrate in the product is 0.0001 to 10 wt. %, preferably 0.005 to 3 wt. %, or wherein the amount of sugar alcohol, preferably mannitol, is 0.0001 to 5 wt. %, preferably 0.005 to 3 wt. %, in the total dermatological or therapeutic product.

Also preferred is that cosmetic composition or cosmetic product according to the invention, wherein the amount of the cosmetic composition or the cosmetic product in the product is 0.0001 to 10 wt. %, preferably 0.005 to 3 wt. % or wherein the amount of sugar alcohol, preferably mannitol, is 0.0001 to 5 wt. %, preferably 0.005 to 3 wt. % in the total cosmetic composition or cosmetic product.

Additionally, it is preferred that in the dermatological or therapeutic product as previous mentioned or cosmetic composition or cosmetic product according to the invention, the amount of the composition, the combined composition, the concentrate, the cosmetic composition or the cosmetic product in the product is 0.0001 to ppm, preferably 0.005 to 3 ppm in the total dermatological or therapeutic product or cosmetic composition or cosmetic product. Furthermore, in the lower effectivity range the amount of sugar alcohol, preferably mannitol, is at least in the range of 0.0001 to 5 ppm, preferably 0.005 to 3 ppm, or higher in the total dermatological or therapeutic product or cosmetic composition or cosmetic product.

In another preferred variation, the invention refers to a non-therapeutic or cosmetic use of a cosmetic composition or a cosmetic product according to the invention for application on, caring, cleansing or protecting the skin and/or the hair.

Preferably the cosmetic compositions or cosmetic products according to the present invention are selected from the group of products for treatment, protecting, care and cleansing of the skin and/or hair or as a make-up product, as a leave-on or rinse-off product, most preferably as leave-on product.

The formulations according to the invention are preferably in the form of an emulsion.

Hereby it is even more preferred for the formulations according to the invention to be a e.g. W/O (water-in-oil)

emulsion, O/W (oil-in-water) emulsion, W/O/W (water-in-oil-in-water) emulsion, O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$-fatty acid, $C_2$-$C_{30}$-esters or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a tonic, a mask, a pencil, stick, roll-on, pump, aerosol (foaming, non-foaming or post-foaming), a deodorant and/or antiperspirant, mouthwash and mouth rinse, a foot care product (including keratolytic, deodorant), an insect repellent, a sunscreen, after sun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a detergent (e.g. soap, synthetic detergent, liquid washing), a solution (e.g. tonic, facial toner or as impregnating solution for wet wipes), a spray (e.g. pump spray or spray with propellant) or a shampoo (including 2-in-1 shampoo, anti-dandruff shampoo, baby shampoo, shampoo for sensitive scalps, concentrated shampoo), conditioner, hair tonic, hair mask or hair water.

Another seventh aspect of the present invention is the cosmetic use of a cosmetic composition or a cosmetic product according to the invention for the reduction of sebum.

A further eighth aspect of the present invention is the use of a pharmaceutical composition or a pharmaceutical product, according to the invention for the:
a) stimulation of cutaneous junctions,
b) stimulation of cutaneous antimicrobial peptides,
c) reduction of COX-2 gene expression and prostaglandin mediated effects,
d) reduction of post-inflammatory hyperpigmentation,
e) stimulation of filaggrin.

Preferably, a cosmetic composition or a cosmetic product, according to the invention is used cosmetically:
a) for improvement of epidermal integrity of the skin,
b) for prevention of external stimuli such as air pollution or particulate matter induced effects,
c) for prevention of skin barrier dysfunction.

An even more preferred variation is the pharmaceutical composition or pharmaceutical product or the cosmetic composition or cosmetic product according to the invention, further comprising one or more of the following: other sebum reducing agents and/or anti-acne agents.

An alternative preferred variation is the pharmaceutical composition or pharmaceutical product according to the invention, further comprising one or more of the following: other sebum reducing agents, anti-acne agents, anti-dandruff agents, other anti-inflammatory agents, TRPV1 antagonists, anti-itch agents, anti-microbial agents, especially anti-Propioni-bacterium *acnes* agents, anti-*Malassezia* agents.

In formulations, the sugar alcohol or the sugar alcohol (16 wt. % in the overall composition) and the *Tetraselmis* extract (dried) or the sugar alcohol and niacinamide, preferably mannitol may be combined with other sebum reducers and/or anti-acne agents especially if these act via different pathways as thus a more pronounced activity can be expected. Since the seborrhoeic condition of the skin is an ideal nutrient medium for bacterial and fungal growth and consequently for e.g. the development of impure skin or acne, a composition for prophylaxis and/or treatment of oily skin is likewise a preferred composition for prophylaxis and/or treatment of impure skin or acne. Suitable agents are e.g. retinoids like 13-cis retinoic acid (isotretinoin), all-trans-retinoic acid, adapalene, their salts or derivatives, androgen inhibitors like spironolactone and cyproterone, antibiotics, preferably clindamycin, erythromycin and tetracycline, zinc or zinc salts, and antiandrogens, 5-alpha-reductase inhibitors, D-panthenol, alpha-hydroxy acids, such as e.g. salicylic acid and lactic acid, pyruvic (alfa-keto acid) acids, aliphatic dicarboxylic acids, such as e.g. azelaic acid, L-carnitine, bakuchiol, 1,2-decanediol, senkyunolide-A and senkyunolide-A containing *Apium graveolens* seed oil, *Quillaja saponaria* extract, *Enantia chlorantha* bark extract, *Spiraea ulmaria* extract, butyl avocate, vitamin B6 (also known as pyridoxine) or its salts or derivatives, vitamin B3 (also known as niacin or nicotinic acid) or its salts or derivatives, benzoylperoxide, phloretin, *Camellia sinensis* extract and contained polyphenols such as e.g. epigallocatechin-3-gallate, red clover (*Trifolium* pretense) extract, soybean (*Glycine Soja*) seed extract, isoflavonoids or isoflavonoid containing extracts, preferably biochanin A, genistein, daidzein, genistin, and daizin.

The abovementioned product groups, preferably in combination with the preferred auxiliary substances, additives and/or active compounds for formulations for the reduction of the sebum concentration of the skin are also preferred as formulations for prophylaxis and/or treatment of oily skin, impure skin or acne.

We presently also disclose a pharmaceutical composition or a pharmaceutical product according to the previously described aspects and variations thereof for use as a medicament in the treatment of any disease as described herein according to the invention, in particular for skin diseases.

We presently also disclose a cosmetic composition, or a cosmetic product as mentioned above for use in a non-therapeutic application as described herein according to the invention, in particular for skin protection.

A preferred cosmetic or therapeutic dermatological formulation for topical application comprises the following constituents or consists of the following: an amount of one or more sugar alcohols 16 wt. % in the overall composition and *Tetraselmis*, in particular *Tetraselmis suecica*, or one or more sugar alcohols or one or more sugar alcohols and niacinamide, preferably wherein the sugar alcohol is mannitol, which is sufficient to reduce the sebum concentration of the skin as well as one or more active compounds. More preferably said formulation comprises a combination of two, three or four active compounds.

Preferably, the active compounds are chosen from one or more of the compound classes in the following group: antiandrogens, isoflavonoid containing extracts, retinoids, vitamins, organic peroxides, organic ethers, organic acids or alcohols.

More preferably, the active components are chosen from: 1,2-decanediol, bakuchiol, salicylic acid; lactic acid; azelaic acid; retinoids, preferably 13-cis retinoic acid (isotretinoin), all-trans-retinoic acid, adapalene, their salts or derivatives; benzoyl peroxide; D-panthenol, vitamin B6 (also known as pyridoxine) or its salts e.g. pyridoxine·HCl or derivatives, vitamin B3 (also known as niacin or nicotinic acid) or its salts or derivatives, butyl avocadate, farnesol; phenoxyethanol; red clover (*Trifolium* pretense) extract, isoflavonoids or isoflavonoid containing extracts, preferably biochanin A, genistein, daidzein, genistin and daizin, and antiandrogens, preferably 5-alpha-reductase inhibitors.

Even more preferably, the one or more active compounds are chosen from the group consisting of: 1,2-decanediol, salicylic acid, lactic acid, azelaic acid, benzoyl peroxide, D-panthenol, 13-cis retinoic acid (isotretinoin), all-trans-retinoic acid, adapalene, their salts or derivatives, bakuchiol, erythromycin, sulfur, butyl avocadate, farnesol, phenoxyethanol, pyridoxine·HCl, red clover (*Trifolium* pretense) extract, biochanin A, genistein, daidzein, genistin, daizin and 5alpha-reductase inhibitor.

Even more preferred, the one or more active compounds are chosen from the group consisting of: 1,2-decanediol, salicylic acid, azelaic acid, benzoyl peroxide, D-panthenol, 13-cis retinoic acid (isotretinoin), all-trans-retinoic acid, adapalene, their salts or derivatives, bakuchiol, erythromycin, butyl avocadate, phenoxyethanol, pyridoxine·HCl, red clover (*Trifolium* pretense) extract, biochanin A, genistein, daidzein, and 5-alpha-reductase inhibitor.

Most preferred, the one or more active compounds are chosen from the group consisting of: 1,2-decanediol, salicylic acid, azelaic acid, benzoyl peroxide, D-panthenol, adapalene, bakuchiol, erythromycin, butyl avocadate, pyridoxine HCl, and biochanin A.

Furthermore, it is highly preferred to include niacinamide as an active compound.

Preferably the one or more active compounds are combined with anti-dandruff active agents. A more pronounced overall effect is found especially if these act via different biological pathways. Anti-dandruff agents may be one material, or a mixture selected from the groups consisting of: azoles, such as climbazole, ketoconazole, itraconazole, econazole, and elubiol; hydroxy pyridones, such as octopirox (piroctone olamine), ciclopirox, rilopirox, and MEA-hydroxyoctyloxypyridinone; kerolytic agents, such as salicylic acid and other hydroxy acids; strobilurins such as azoxystrobin and metal chelators such as 1,10-phenanthroline.

In an embodiment, the azole anti-microbials is an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof.

In an embodiment, the preferred anti-dandruff agents may be present in an amount from 0.1 wt. % to 10 wt. %, in a further embodiment from 0.25 wt. % to 8 wt. %, in yet a further embodiment from 0.5 wt. % to 6 wt. %.

In compositions and products according to the invention, the sugar alcohol and *Tetraselmis* extract, or one or more sugar alcohols themselves or one or more sugar alcohols and niacinamide in combination, may also be further combined with anti-inflammatory or anti-irritant agents, preferably if these agent act via different pathways than COX-2/PGE2 and/or anti-acne agents and/or anti-microbial agents effecting acne-related *P. acnes* and/or dandruff related *Malassezia* sp. These combinations are especially beneficial if the formulation is intended for use on impure, acne-prone or acne oily skin or sensitive oily skin or sensitive oily scalp or dandruff.

The compositions and products of the invention may contain anti-inflammatory and/or redness and/or itch ameliorating ingredients, in particular steroidal substances of the corticosteroid type selected from the group consisting of hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Non-steroidal anti-inflammatories can also be used. Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid derivatives, in particular avenanthramides described in WO 2004 047833 A1, are preferred anti-itch ingredients in a composition according to the present invention.

Also useful are natural or naturally occurring anti-inflammatory/anti-irritant mixtures of substances or mixtures of substances that alleviate inflammation and/or reddening and/or itching, in particular extracts or fractions from camomile, Aloe vera, *Commiphora* species, *Rubia* species, willow, willow-herb, oats, calendula, *arnica*, St John's wort, honeysuckle, rosemary, *Passiflora incarnata*, witch hazel, ginger or *Echinacea*; preferably selected from the group consisting of extracts or fractions from camomile, Aloe vera, oats, calendula, *arnica*, honeysuckle, rosemary, witch hazel, ginger or *Echinacea*, and/or pure substances, natural alpha-bisabolol, synthetic bisabolol, apigenin, apigenin-7-glucoside, gingerols, shogaols, gingerdiols, dehydrogingerdiones, paradols, especially natural or synthetic 6-paradol, naturally occuring avenanthramides, preferably avenanthramide A, avenanthramide B, avenanthramide C, avenanthramide D, avenanthramide E, non-natural or non-naturally occuring avenanthramides, preferably dihydroavenanthramide D, dihydroavenanthramide E, tranilast, boswellic acid, phytosterols, glycyrrhizin, glabridin, sclareolide and licochalcone A; preferably selected from the group consisting of natural alpha-bisabolol, synthetic bisabolol, natural avenanthramides, non-natural avenanthramides, preferably dihydroavenanthramide D (as described in WO 2004 047833 A1), ginger extract, gingerols, shogaols, gingerdiols, dehydrogingerdiones, paradols, especially natural or synthetic 6-paradol, boswellic acid, phytosterols, glycyrrhizin, and licochalcone A, and/or allantoin, sclareolide, panthenol, (pseudo-)ceramides [preferably Ceramide 2, hydroxypropyl bispalmitamide M EA, cetyloxypropyl glyceryl methoxypropyl myristamide, N—(I-hexadecanoyl)-4-hydroxy-L- proline (1-hexadecyl) ester, hydroxyethyl palmityl oxyhydroxypropyl palmitamide], phytosterols, chitosan, and β-glucans, in particular 1,3-1,4-glucan from oats.

The total amount of anti-irritants or anti-inflammatory substances in a formulation or product according to the invention is preferably in the range of from 0.0001 to 20 wt. %, preferably from 0.0001 to 10 wt. %, in particular from 0.001 to 5 wt. %, based on the total weight of the formulation or product, respectively.

Transient receptor potential cation channel subfamily V member 1 (TRPV1) antagonists Suitable compounds that can be combined with the products of the invention are such which reduce the hypersensitivity of skin nerves based on their action as TRPV1 antagonists, these encompass preferably e.g. trans-4-tert-butyl cyclohexanol as described in WO 2009 087242 A1, or indirect modulators of TRPV1 by an activation of the µ-receptor, e.g. acetyl tetrapeptide-15.

Sugar alcohols in amount of ≥16 wt. % in the overall composition and *Tetraselmis* extract (preferably *Tetraselmis suecica*), or one or more sugar alcohols themselves, such as mannitol, or one or more sugar alcohols and niacinamide, in the inventive formulations may also be combined with anti-dandruff agents. Suitable anti-dandruff agents are Pirocton Olamin (1-hydroxy-4-methyl-6-(2,4,4-trimethylpentyl)-2-(1H)-pyridinone monoethanolamine salt), Baypival (Climbazole), Ketoconazol® (2RS,4SR)-1-(4-{4-[-2-(2,4-Dichlorphenyl)-2-(imidazol-1-ylmethyl)-1,3-dioxolan-4-yl-methoxy]phenyl}piperazin-1-yl)ethanon, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon S (protein/undecylenic acid condensate), zinc pyrithione, aluminium pyrithione and magnesium pyrithione/dipyrithione magnesium sulfate.

A further preferred cosmetic formulation for topical application comprises the following constituents or consists of the following constituents:
- an amount of sugar alcohol 16 wt. % in the overall composition and an *Tetraselmis* extract (preferably *Tetraselmis suecica*), preferably wherein the sugar alcohol is mannitol, which is sufficient to reduce the sebum concentration of the skin;
- one, two, three, four, five, six, seven, eight, nine, ten or more, preferably two or more, more preferably three or more cleansing auxiliary substances;
- optionally one or more further auxiliary substances and/or additives.

Such a cosmetic formulation is particularly suitable for cleansing greasy-oily and/or impure skin.

Another preferred cosmetic formulation for topical application comprises the following constituents or consists of the following constituents:
- niacinamide and one or more sugar alcohols, preferably mannitol which is sufficient to reduce the sebum concentration of the skin;
- one, two, three, four, five, six, seven, eight, nine, ten or more, preferably two or more, more preferably three or more cleansing auxiliary substances;
- optionally one or more further auxiliary substances and/or additives.

Such a cosmetic formulation has a particularly long shelf life.

An even more preferred cosmetic formulation for topical application comprises the following constituents or consists of the following constituents:
- one or more sugar alcohols, preferably mannitol which is sufficient to reduce the sebum concentration of the skin;
- one, two, three, four, five, six, seven, eight, nine, ten or more, preferably two or more, more preferably three or more cleansing auxiliary substances;
- optionally one or more further auxiliary substances and/or additives.

Such a cosmetic formulation has a particularly good availability.

In formulations, the inventive sugar alcohol with *Tetraselmis* extracts or one or more sugar alcohols, preferably mannitol with niacinamide or one or more sugar alcohols, preferably mannitol, for themselves may also be combined with film formers especially as these provide an additional topical, physical barrier to protect the skin. They will add to the epidermal-integrity-improving effect of *Tetraselmis* extract, which is especially beneficial as external stimuli such as e.g. PM were shown to increase sebum production and lead to barrier dysfunction.

Typical film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof, beta-glucans like 1,3-1,4-glucan from oats or 1,3-1,6-glucans from yeasts or mushrooms and similar compounds.

Sugar alcohols and niacinamide are both colorless and odorless compounds; furthermore both are readily water soluble and allow thus broad application in all different kind of cosmetic formulations. Additionally, sugar alcohols and niacinamide are solids available typically in powder form.

To make a synergistic combination even more easily to formulate the pharmaceutical or cosmetic compositions or products according to the present invention, they are used in a liquid carrier system. To prepare such liquid formulations of a sugar alcohol and niacinamide, the solid ingredients, i.e. sugar alcohol and niacinamide, are dissolved under stirring at ambient temperature (20-30° C.) in a liquid carrier system giving a colorless solution. As liquid carrier preferably glycerin, 1,3-butylene glycol 1,3-propanediol, 1,2-pentanediol or water or mixtures thereof is used.

Thus, in a still further aspect the present invention relates to a liquid formulation, comprising one or more sugar alcohol(s) or a combination of one or more sugar alcohol(s) and niacinamide which is used for the preparation of the pharmaceutical or cosmetic compositions or products according to the present invention.

In particular, such a liquid formulation comprises:
a) 0.5 to 25 wt. %, preferably 1 to 20 wt. %, sugar alcohol;
b) optionally 1 to 35 wt. %, preferably 2 bis 20 wt. %, niacinamide;
c) 5 to 55 wt. %, preferably 10 to 50 wt. %, liquid carrier; and
d) optionally 0.1 to 5 wt. % of one or more preservative or preservative system.

Particularly preferred is a liquid formulation comprising:
a) 1 to 20 wt. % sugar alcohol selected from mannitol, sorbitol, xylitol, erythritol, maltitol, inositol and mixtures thereof;
b) optionally 2 bis 20 wt. % niacinamide;
c) 10 to 50 wt. % liquid carrier selected from glycerin, 1,3-butylene glycol, 1,3-propanediol, 1,2-pentanediol and mixtures thereof; and
d) optionally 0.1 to 5 wt. % of one or more preservative or preservative system.

Compositions of said liquid formulations are specified in Table 9 below.

The liquid formulations, comprising one or more sugar alcohol(s) or a combination of one or more sugar alcohol(s) and niacinamide are used for the preparation of the pharmaceutical or cosmetic products or the dermatological or therapeutic products according to the present invention.

EXPERIMENTAL SECTION

Example 1: Preparation of a *Tetraselmis suecica* Extract 3 g freeze-dried *Tetraselmis suecica* biomass and 30 g of water were mixed and stirred for 2 hours at 80° C. The liquid extract was separated from the biomass, 30 g of water was added to the extracted biomass and the mixture was stirred for another 2 hours at 80° C. The liquid was separated from the biomass by centrifugation, both extract solutions were combined, and the water was removed by freeze-drying. The extractions were performed with 3 different biomass batches.

For comparison, an aqueous extract according to the description in US2010143267 A1 was prepared from the same 3 biomass batches and water was removed by freeze-drying.

TABLE 1

*Tetraselmis suecica* extract obtained by extraction at room temperature and at 80° C.

| Condition of extraction | Mean yield | Appearance |
|---|---|---|
| 80° C. | 38.4 ± 0.2% | Beige greenish solid |
| Room temperature (18 to 23° C.) | 40.0 ± 0.9% | Intensive dark green solid |

Extraction upon heating gives a well comparable, very slightly lower, high extraction yield when compared to extraction at room temperature, but it surprisingly gives a much lighter colored extract which is especially advantageous for the use as cosmetic ingredient as consumers prefer low colored products. Heat treatment furthermore has the additional advantage that enzymes in the biomass are inactivated which is especially advantageous when using viable or non-inactivated biomass. Additionally, microbiological contamination by bacteria, fungi or yeasts, which is especially challenging for extractions with water or extractant systems with high water content at low temperatures is prevented by extracting at higher temperatures (>50° C.).

TABLE 2

Composition of *Tetraselmis suecica* extracts obtained by extraction at 80° C. and at Room temperature

| Substance class | Mean content [wt.-%] (Extract obtained at 80° C.) | Mean content [wt.-%] (Extract obtained at Room temperature (18 to 23° C.)) |
|---|---|---|
| Sum of minerals Containing but not limited to: | 20.3 ± 0.6 | 21.4 ± 0.8 |
| Sodium Na$^+$ | 5.7 ± 0.2 | 5.7 ± 0.3 |
| Potassium K$^+$ | 3.6 ± 0.1 | 3.6 ± 0.2 |
| Magnesium Mg$^{2+}$ | 0.7 ± 0.1 | 0.7 ± 0.0 |
| Calcium Ca$^{2+}$ | 0.8 ± 0.1 | 0.9 ± 0.0 |
| Chloride Cl$^-$ | 6.9 ± 0.2 | 7.1 ± 0.2 |
| Sulfate SO$_4^{2-}$ | 2.1 ± 0.1 | 2.6 ± 0.1 |
| Phosphate PO$_4^{3-}$ | 0.4 ± 0.2 | 0.9 ± 0.4 |
| Mannitol | 11.8 ± 0.9 | 11.6 ± 0.7 |
| Total galactose (free and bound)* | 9.7 ± 0.7 | 7.8 ± 0.4 |
| Total glucose (free and bound)* | 7.0 ± 0.8 | 3.5 ± 0.0 |
| Sum of amino acids Containing but not limited to: | 8.4 ± 0.8 | 9.2 ± 0.7 |
| Glutamic acid | 2.88 ± 0.30 | 2.77 ± 0.27 |
| Alanine | 1.11 ± 0.08 | 1.10 ± 0.10 |
| Arginine | 0.80 ± 0.30 | 0.17 ± 0.02 |
| Ornithine | 0.54 ± 0.28 | 1.26 ± 0.17 |
| Citruline | 0.53 ± 0.23 | 0.74 ± 0.03 |
| Asparagine | 0.39 ± 0.04 | 0.19 ± 0.02 |
| Taurine | 0.39 ± 0.04 | 0.35 ± 0.04 |
| Lysine | 0.37 ± 0.04 | 0.49 ± 0.02 |
| Aspartic acid | 0.27 ± 0.10 | 0.76 ± 0.03 |
| Proline | 0.14 ± 0.02 | 0.18 ± 0.02 |
| Glutamine | 0.12 ± 0.06 | 0.07 ± 0.02 |
| Total Nitrogen** | 4.22 ± 0.17 | 4.91 ± 0.16 |

*determined after hydrolysis and derivatization by GC
**determined by nitrogen analyzer Example 2: Preparation of a Liquid Version of Sugar Alcohol with *Tetraselmis suecica* Extract To 4.6 g *Tetraselmis suecica* extract dry matter, obtained by extraction at 80° C. according to Example 1, 97 g water, 46 g glycerin, 18 wt. % mannitol, 0.5% sodium benzoate and 0.2% potassium sorbate (both based on the total weight of the liquid mixture) were added, and the pH of the mixture was adjusted with help of lactic acid to 4.5 giving a beige to light brownish solution.

Example 3: Effect of *Tetraselmis suecica* Extract (Dried) on the Total Lipid Content of Ex Vivo Human Sebaceous Glands Organ culture of human sebaceous glands micro-dissected from human skin explants was performed to evaluate the modulatory activity of *Tetraselmis suecica* extract prepared according to the description given in Example 1 on the sebum level. The extract is employed in the dried form.

After removal of the epidermis of the full thickness skin sample, the sebaceous glands were carefully removed using micro-scissors and scalpel. The micro-dissected sebaceous glands were then pooled in groups of 8 and cultured up to day 6 in a 24 well plate immersed in 500 µl of modified Williams'E medium. After 24 hours of acclimation the culture medium was changed and substituted with the medium containing the extract to be tested. The medium was renewed at day 3 and 5 of culture. At day 6 the glands were collected and used for the quantification of lipids and proteins. In order to make the estimated productivity of the glands comparable, which are variable in biomass, their total sebum content was estimated and divided by the proteins extracted from the gland tissue, obtaining the ratio between the produced sebum and the tissue proteins (i.e. mg of lipids/mg of proteins).

To do so, each sebaceous glands group was homogenized in 100 µl of isopropyl alcohol to extract lipids and let the proteins undissolved. After centrifugation the supernatant containing the extracted sebum was collected and analyzed. The remaining pellet was dried using a vacuum dry evaporator and then minced in presence of 50 µl of protein lysis buffer. After an appropriate incubation time, this extractive mixture was centrifuged, and the supernatant was collected and analyzed. The lipids dissolved in isopropyl alcohol and the proteins dissolved in the lysis buffer were quantified by infrared spectroscopy using a Direct Detect IR Spectrometer (Millipore). The total lipid amount was obtained by normalizing the quantified lipids upon the quantified proteins (i.e. mg of lipids/mg of proteins). The amounts of normalized lipids, i.e. the sebum produced by each group of sebaceous glands, obtained from the treated groups was compared to that of the untreated control group and the modulatory activity was calculated in percentage. As positive control, a 5 µM Capsaicin treatment was included in the experimental design. Capsaicin is an active component of chili peppers suitable to inhibit sebogenesis [Tóth et al., J. Invest. Derm. (2009), 129: 329-339]. For statistical analysis, differences among groups were evaluated by one-way anova with permutation test followed by Dunnett's permutation test.

To better understand the response to the extract, a viability test was performed in parallel at day 1 and day 6 of organ culture. Resazurin was added to the wells (1:11) and let incubate for 2 hours. At the end of the incubation an aliquot of the medium was read with a fluorometer (excitation: 560 nm, emission: 590 nm). The medium was then replaced with normal medium for 2 hours in order to eliminate residual resazurin. After this the medium was replaced again with medium containing the test samples. The viability in each well was measured as the difference in percentage between day 6 and day 1.

To evaluate donor responsiveness and interindividual variability the extract was tested on sebaceous glands obtained from skin samples of three different donors.

Table 3: Effect of *Tetraselmis suecica* water-extract (dried) on lipids and viability of micro-dissected human sebaceous glands In the present cell tests, ex vivo and in vitro, and generally for biological tests, the dried form of the *Tetraselmis* extract is employed to avoid side effects resulting from solvents, glycerin or the preservative system.

| Parameter | Test sample | Donor 1 | Donor 2 | Donor 3 |
|---|---|---|---|---|
| Reduction of lipids at day 6 versus untreated [%]* | 5 µM (=1.5 ppm) Capsaicin | 11 | 28 | 14 |
| | 0.3 ppm extract (extraction at 80° C.) | 19 | 33 | 18 |
| Viability [%] | Untreated | 93 | 100 | 81 |
| | 5 µM (1.5 ppm) Capsaicin | 92 | 99 | 85 |
| | 0.3 ppm extract (extraction at 80° C.) | 108 | 101 | 83 |

*All results were statistically significant versus untreated with $p < 0.01$

The results show that *Tetraselmis suecica* water extract (dried) obtained by extraction at 80° C. is surprisingly a highly effective reducer of the normalized total lipids, i.e. sebum content of human sebaceous glands without affecting their viability. It is more effective than the positive control capsaicin and this even at a 5-fold lower concentration. Furthermore, the sebaceous glands obtained from all three donors responded to the extract (donor responsiveness: 100%).

Similar effects were also achieved in comparing the mannitol and *Tetraselmis* extract combination as prepared according to Example 2. The combination of mannitol with *Tetraselmis suecica* water extract (dried) is a particularly highly effective reducer of the normalized total lipids, i.e. sebum content of human sebaceous glands without affecting their viability. It is more effective than the positive control capsaicin. Moreover, the further addition of niacinamide shows good skin moisturizing effects.

Example 4: Effect of Mannitol (Alone) on the Total Lipid Content of Ex Vivo Human Sebaceous Glands The Organ culture of human sebaceous glands microdissected from human skin explants was performed to evaluate the modulatory activity of mannitol on the sebum level.

After removal of the epidermis of the full thickness skin sample, the sebaceous glands were carefully removed using micro-scissors and scalpel. The micro-dissected sebaceous glands were then pooled in groups of 8 and cultured up to day 6 in a 24 well plate immersed in 500 µl of modified Williams'E medium. After 24 hours of acclimation the culture medium was changed and substituted with the medium containing the sample to be tested. The medium was renewed at day 3 and 5 of culture. At day 6 the glands were collected and used for the quantification of lipids and proteins. In order to make the estimated productivity of the glands comparable, which are variable in biomass, their total sebum content was estimated and divided by the proteins extracted from the gland tissue, obtaining the ratio between the produced sebum and the tissue proteins (i.e. mg of lipids/mg of proteins).

To do so, each sebaceous glands group was homogenized in 100 µl of isopropyl alcohol to extract lipids and let the proteins undissolved. After centrifugation the supernatant containing the extracted sebum was collected and analyzed. The remaining pellet was dried using a vacuum dry evaporator and then minced in presence of 50 µl of protein lysis buffer. After an appropriate incubation time, this extractive mixture was centrifuged, and the supernatant was collected and analyzed. The lipids dissolved in isopropyl alcohol and the proteins dissolved in the lysis buffer were quantified by infrared spectroscopy using a Direct Detect IR Spectrometer (Millipore). The total lipid amount was obtained by normalizing the quantified lipids upon the quantified proteins (i.e. mg of lipids/mg of proteins). The amounts of normalized lipids, i.e. the sebum produced by each group of sebaceous glands, obtained from the treated groups was compared to that of the untreated control group and the modulatory activity was calculated in percentage. As positive control, a 5 µM Capsaicin treatment was included in the experimental design. Capsaicin is an active component of chili peppers suitable to inhibit sebogenesis [Tóth et al., J. Invest. Derm. (2009), 129: 329-339]. For statistical analysis, differences among groups were evaluated by one-way anova with permutation test followed by Dunnett's permutation test.

To better understand the response to the extract, a viability test was performed in parallel at day 1 and day 6 of organ culture. Resazurin was added to the wells (1:11) and let incubate for 2 hours. At the end of the incubation an aliquot of the medium was read with a fluorometer (excitation: 560 nm, emission: 590 nm). The medium was then replaced with normal medium for 2 hours in order to eliminate residual resazurin. After this the medium was replaced again with medium containing the test samples. The viability in each well was measured as the difference in percentage between day 6 and day 1.

TABLE 4

Effect of mannitol on lipids and viability of micro-dissected human sebaceous glands

| Parameter | Test sample | Total lipid reduction [%] |
|---|---|---|
| Reduction of lipids at day 6 versus untreated [%]* | 5 µM (1.5 ppm) Capsaicin | −25 |
| | 0.03 ppm mannitol** | −17 |
| Viability [%] | Untreated | 84 |
| | 5 µM (1.5 ppm) Capsaicin | 82 |
| | 0.03 ppm mannitol | 81 |

*All results were statistically significant versus untreated with p < 0.01
**D-Mannitol, Sigma-Aldrich M4125 (≥98%)

The results clearly show that mannitol surprisingly significantly reduces the lipid content of ex vivo human sebaceous glands.

According to Example 1, *Tetraselmis suecica* water extract (dried) contains 11.8±0.9 wt. % of mannitol. The extract reduced the total lipid content at 0.3 ppm significantly and was always more effective than 5 µM capsaicin when tested in three separate experiments (Example 3).

The 0.03 ppm mannitol corresponds to the mannitol content in 0.3 ppm *Tetraselmis suecica* water extract (dried). The 0.03 ppm mannitol significantly reduced the sebum content but less effectively than 5 µM capsaicin, thus, indicating that mannitol is part of the active principles/ingredients of *Tetraselmis suecica* extract but is not solely responsible for the observed sebum reducing effect of the extract. Other extract constituents enhance the observed sebum reducing efficacy of the extract in an additive or synergistic manner.

Example 5: Effect of Mannitol on the Gene Expression of Claudin 7

Neonatale humane epidermal keratinocytes (nHEK) were cultivated in EpiLife medium (Gibco) including HKGS-Kit (Gibco) at 5% $CO_2$ at 37° C. according to the supplier instructions.

The cells were treated for 24 hours with *Tetraselmis suecica* water extract obtained according to Example 1 by extracting at 80° C. at 0.025% or medium as vehicle control. Genomic target expression levels in extract treated cells were measured by RT-qPCR comparing to medium treatment.

RNA isolation took place using RNeasy® Mini Kit, Qiagen. Total RNA concentrations were measured using µCuvetteG 1.0 and BioPhotometer, Eppendorf by measuring the absorption at 260 nm. Purity control values, like E260/280 and E 260/230 were calculated simultaneously. Reverse transcription was done using high capacity RNA-to-cDNA Kit, Applied Biosystems, according to the supplier instructions. Samples were treated in the PCR Thermocycler, Biometra.

For the fast real-time PCR, cDNA was diluted with RNase-free water and TaqMan™ Fast Universal PCR Master Mix, Applied biosystems. Quantitaive Real-Time PCR was done using StepOne Plus Fast Real Time PCR Instrument, Applied biosystems. Analysis was done with StepOne-Software and 2-ΔCT Method (normalized to endogenous control HTRP1 expression).

For upregulations RQ values ≥2.0 and for downregulations RQ values <0.5 are considered to be relevant.

TABLE 5

Effect of mannitol on claudin 7

| | | RQ value | |
|---|---|---|---|
| Gene | Relevance | 0.025% *Tetraselmis* extract (containing ca. 0.002% Mannitol) | 0.002% Mannitol |
| CLDN1 [Claudin 1] | Tight junctions | 4.0 | 0.5 |
| CLDN7 [Claudin 7] | Tight junctions | 2.0 | 2.0 |
| OCLN [Occludin] | Tight junctions | 4.0 | 1.0 |
| CGN [Cingulin] | Tight junctions | 4.0 | 1.0 |

The results show that mannitol alone or also the combination of *Tetraselmis* extract containing mannitol surprisingly upregulate the claudin 7 gene involved in tight junctions.

Furthermore, other genes, such as claudin 1, occludin or cingulin, also involved in tight junctions are synergistically upregulated by the combination of *Tetraselmis* extract containing mannitol. Therefore, a differentiation of the effect by treatment with *Tetraselmis* extract and by the treatment with mannitol is shown.

Example 6: Effect of Erythritol, Xylitol and Sorbitol on the Total Lipid Content of Ex Vivo Human Sebaceous Glands Organ culture of human sebaceous glands micro-dissected from human skin explants was performed as described in Example 4 to evaluate the modulatory activity of erythritol (C4 sugar alcohol), xylitol (C5 sugar alcohol) and sorbitol (C6 sugar alcohol) on the sebum level. 5 µM Capsaicin was tested in parallel as reference/positive control.

TABLE 6

Effect of erythritol, xylitol and sorbitol on lipids and viability of micro-dissected human sebaceous glands

| Parameter | Test sample | Results |
|---|---|---|
| Reduction of lipids at day 6 versus untreated [%]* | 5 µM (1.5 ppm) Capsaicin | −21 |
| | 0.05 ppm erythritol** | −26 |
| | 0.5 ppm erythritol** | −36 |
| | 0.05 ppm xylitol*** | −23 |
| | 0.5 ppm xylitol*** | −46 |
| | 0.05 ppm sorbitol**** | −16 |
| | 0.5 ppm sorbitol**** | −40 |
| Viability [%] | Untreated | 89 |
| | 5 µM (1.5 ppm) Capsaicin | 89 |
| | 0.05 ppm erythritol** | 82 |
| | 0.5 ppm erythritol** | 77 |
| | 0.05 ppm xylitol*** | 86 |
| | 0.5 ppm xylitol*** | 80 |
| | 0.05 ppm sorbitol**** | 80 |
| | 0.5 ppm sorbitol**** | 78 |

*All results were statistically significant versus untreated with p < 0.01
**meso-Erythritol, Sigma E7500 (≥99%), CAS number 149-32-6
***Xylitol, Sigma X3375 (≥99%), CAS number 87-99-0
****D-Sorbitol, Aldrich 240850 (99%), CAS number: 50-70-4

The results clearly show that erythritol, xylitol and sorbitol surprisingly significantly reduces the lipid content of ex vivo human sebaceous glands. All three sugar alcohols are more active than the positive control/reference capsaicin.

None of the test samples has relevantly impacted sebaceous glands viability.

Example 7: Effect of Threitol, Inositol, Lactitol, and Maltitol on the Total Lipid Content of Ex Vivo Human Sebaceous Glands Organ culture of human sebaceous glands micro-dissected from human skin explants was performed as described in example 4 to evaluate the modulatory activity of threitol, inositol, lactiol and maltitol on the sebum level. 5 µM Capsaicin was tested in parallel as reference/positive control.

TABLE 7

Effect of threitol, inositol, lactitol and maltitol on lipids and viability of micro-dissected human sebaceous glands

| Parameter | Test sample | Results |
|---|---|---|
| Reduction of lipids at day 6 versus untreated [%]* | 5 µM (1.5 ppm) Capsaicin | −20 |
| | 0.05 ppm threitol** | −31 |
| | 0.5 ppm threitol** | −47 |
| | 0.05 ppm inositol*** | −32 |
| | 0.5 ppm inositol*** | −10 |
| | 0.05 ppm lactitol**** | −22 |
| | 0.5 ppm lactitol**** | −22 |
| | 0.05 ppm maltitol***** | −44 |
| | 0.5 ppm maltitol***** | −39 |
| Viability [%] | Untreated | 92 |
| | 5 µM (1.5 ppm) Capsaicin | 91 |
| | 0.05 ppm threitol** | 84 |
| | 0.5 ppm threitol** | 82 |
| | 0.05 ppm inositol*** | 91 |
| | 0.5 ppm inositol*** | 97 |
| | 0.05 ppm lactitol**** | 99 |
| | 0.5 ppm lactitol**** | 100 |
| | 0.05 ppm maltitol***** | 79 |
| | 0.5 ppm maltitol***** | 80 |

*All results were statistically significant versus untreated with $p < 0.01$
**D-Threitol, Aldrich 377619 (99%), CAS number 2418-52-2
***myo-Inosiitol, Sigma I5125 (≥99%), CAS number 87-89-8
****Lactitol, Sigma-Aldrich 19346 (≥98%), CAS number 585-86-4
*****Maltitol, Sigma M8892 (≥98%), CAS number 585-88-6

The results clearly show that threitol, inositol, lactitol and maltitol surprisingly significantly reduce the lipid content of ex vivo human sebaceous glands. All four sugar alcohols are more active than the positive control/reference capsaicin.

None of the test samples has relevantly impacted sebaceous glands viability.

Example 8: Synergistic Effect of Sugar Alcohol and Niacinamide on the Total Lipid Content of Ex Vivo Human Sebaceous Glands The same experimental set-up as described in Example 4 was used to evaluate the combination of the sugar alcohol sorbitol and niacinamide for synergistic activity. 5 µM Capsaicin was tested in parallel as reference/positive control.

Kull's equation for calculation of the synergism index SI was used:

$$SI = C \times D/A + C \times E/B$$

With
A=lipid reduction by sorbitol at concentration x
B=lipid reduction by niacinamide at concentration y
C=lipid reduction by the combination of sorbitol at concentration x/2 and niacinamide at concentration y/2
D=Factor for sorbitol=>0.5 (due to half concentration tested in the combination)
E=Factor for niacinamide=>0.5 (due to half concentration tested in the combination)

A SI=1 is obtained for additive activity of the two combined components, whereas a SI<1 proves antagonistic activity (observed efficacy is lower than additive) and SI>1 proves synergistic activity (observed efficacy is higher than additive). Results of this experiment are summarized in Table 8.

TABLE 8

Effect of sorbitol and niacinamide on the total lipid content of ex vivo human sebaceous glands

| Parameter | Test sample | Lipid reduction [%] |
|---|---|---|
| Reduction of lipids at day 6 versus untreated [%]* | 5 µM (1.5 ppm) capsaicin | 13* |
| | 0.5 ppm sorbitol** | 11* |
| | 0.5 ppm niacinamide*** | 2 |
| | 0.25 ppm sorbitol + 0.25 ppm niacinamide | 15* |
| Viability [%] | Untreated | 99 |
| | 5 µM (1.5 ppm) capsaicin | 95 |
| | 0.5 ppm sorbitol | 95 |
| | 0.5 ppm niacinamide | 100 |
| | 0.25 ppm sorbitol + 0.25 ppm niacinamide | 98 |

*Results were statistically significant versus untreated with $p < 0.01$
**D-Sorbitol, Aldrich 240850 (99%), CAS number: 50-70-4
***Niacinamide, Nutrilo GmbH (≥99% by HPLC), CAS number: 98-92-0

$$SI = 15 \times 0.5/11 + 15 \times 0.5/2 = 4.43$$

The obtained SI of 4.43 clearly proves that a combination of a sugar alcohol and niacinamide surprisingly exhibits a highly synergistic reduction of the total lipids content, i.e. sebum level of human sebaceous glands.

Niacinamide alone did not show a relevant lipid reducing activity when tested on ex vivo sebaceous glands. Sorbitol exhibited efficacy in the expected range when compared to capsaicin. The combination of both let to an unexpected intensively boosted efficacy.

Cosmetic ingredients ideally possess no own color and odor and thereby have no own impact on the visual appearance and smell of the final cosmetic formulation. Sugar alcohols and niacinamide are both colorless and odorless compounds; furthermore both are readily water soluble and allow thus broad application in all different kind of cosmetic formulations.

Additionally, sugar alcohols and niacinamide are solids available typically in powder form. To make a synergistic combination even more easily to formulate typical cosmetic formulations, they can be used in a liquid carrier system. To prepare liquid combinations, the solid ingredients, i.e. sugar alcohols and niacinamide, are dissolved under stirring at ambient temperature (20-30° C.) in the liquid carrier system giving a colorless solution.

TABLE 9

Formulations containing sugar alcohols and niacinamide in liquid form

| Ingredient | Amount wt.-% | | | | | | | |
|---|---|---|---|---|---|---|---|---|
| | 1 | 2 | 3 | 4 | 5 | 6 | 7 | 8 |
| Mannitol | 5 | | | | 1 | | | 5 |
| Sorbitol | | 20 | | | 5 | | | |
| Xylitol | | | 3 | | | | | 5 |
| Erythritol | | | | 20 | | | | |
| Maltitol | | | | | | 15 | | |
| Inositol | | | | | | | 1 | |
| Niacinamide | 5 | 5 | 1.5 | 2 | 10 | 30 | 20 | 5 |

TABLE 9-continued

Formulations containing sugar alcohols and niacinamide in liquid form

| Ingredient | Amount wt.-% | | | | | | | |
|---|---|---|---|---|---|---|---|---|
|  | 1 | 2 | 3 | 4 | 5 | 6 | 7 | 8 |
| Glycerin |  |  | 35 |  | 25 |  | 50 |  |
| 1,3-Butylene glycol |  |  |  |  |  | 25 |  |  |
| 1,3-Propanediol |  | 20 |  | 30 |  |  |  |  |
| 1,2-Pentanediol | 10 |  |  |  | 10 |  |  | 10 |
| Water |  |  | Ad 100 |  |  |  |  |  |

The liquid formulations can further comprise 0.1 to 5 wt. % of one or more preservative(s) or a preservative system.

The liquid formulations comprising one or more sugar alcohol(s) or a combination of one or more sugar alcohol(s) and niacinamide are used in the preparation of the pharmaceutical or cosmetic products or the dermatological or therapeutic products according to the present invention.

Example 9: Formulation Examples

In formulations 1 to 22 the following two perfume oils PFO1 and PFO2 were each used as fragrance (DPG=dipropylene glycol).

TABLE 10

Perfume oil PFO1 with rose smell (amounts in parts b.w.)

| Component | Amount |
|---|---|
| Acetophenone, 10% in DPG | 10.00 |
| n-Undecanal | 5.00 |
| Aldehyde C14, so-called (peach aldehyde) | 15.00 |
| Allylamyl glycolate, 10% in DPG | 20.00 |
| Amyl salicylate | 25.00 |
| Benzyl acetate | 60.00 |
| Citronellol | 80.00 |
| d-Limonene | 50.00 |
| Decenol trans-9 | 15.00 |
| Dihydromyrcenol | 50.00 |
| Dimethylbenzylcarbinyl acetate | 30.00 |
| Diphenyloxide | 5.00 |
| Eucalyptol | 10.00 |
| Geraniol | 40.00 |
| Nerol | 20.00 |
| Geranium oil | 15.00 |
| Hexenol cis-3, 10% in DPG | 5.00 |
| Hexenyl salicylate cis-3 | 20.00 |
| Indole, 10% in DPG | 10.00 |
| Alpha-ionone | 15.00 |
| Beta-ionone | 5.00 |
| Lilial ® (2-methyl-3-(4-tert-butyl-phenyl)propanal) | 60.00 |
| Linalool | 40.00 |
| Methylphenyl acetate | 10.00 |
| Phenylethyl alcohol | 275.00 |
| Styrolyl acetate | 20.00 |
| Terpineol | 30.00 |
| Tetrahydrolinalool | 50.00 |
| Cinnamyl alcohol | 10.00 |
| Total: | 1,000.00 |

TABLE 11

Perfume oil PFO2 with white blossom and musk smell (amounts in parts b.w.)

| Component | Amount |
|---|---|
| Benzyl acetate | 60.00 |
| Citronellyl acetate | 60.00 |
| Cyclamenaldehyde (2-methyl-3-(4-isopropylphenyl)propanal | 20.00 |
| Dipropylene glycol (DPG) | 60.00 |
| Ethyllinalool | 40.00 |
| Florol (2-isobutyl-4-methyltetrahydro-2H-pyran-4-ol) | 30.00 |
| Globanone ® [(E/Z)-8-cyclohexadecen-1-one] | 180.00 |
| Hedione ® (methyldihydrojasmonate) | 140.00 |
| Hexenyl salicylate, cis-3 | 10.00 |
| Vertocitral (2,4-dimethyl-3-cyclohexenecarboxaldehyde) | 5.00 |
| Hydratropaaldehyde, 10% in DPG | 5.00 |
| Isodamascone (1-(2,4,4-trimethyl-2-cyclohexen-1-yl)-2-buten-1-one, 10% in DPG | 5.00 |
| Isomuscone (cyclohexadecanone) | 40.00 |
| Jacinthaflor (2-methyl-4-phenyl-1,3-dioxolane) | 10.00 |
| Cis-jasmone, 10% in DPG | 20.00 |
| Linalool | 50.00 |
| Linalyl acetate | 30.00 |
| Methyl benzoate, 10% in DPG | 25.00 |
| para-Methyl cresol, 10% in DPG | 10.00 |
| Nerol | 20.00 |
| Phenylpropylaldehyde | 5.00 |
| 2-Phenylethyl alcohol | 82.00 |
| Tetrahydrogeraniol | 13.00 |
| 2,2-Dimethyl-3-cyclohexyl-1-propanol | 80.00 |
| Total: | 1,000.00 |

TABLE 12

Cosmetic formulations 1 to 11 (amounts in parts b.w.)

| Ingredients | 1 | 2 | 3 | 4 | 5 | 6 | 7 | 8 | 9 | 10 | 11 |
|---|---|---|---|---|---|---|---|---|---|---|---|
| Mannitol | 0.3 |  |  |  |  | 0.1 |  |  | 0.7 |  |  |
| Sorbitol |  | 1 |  |  |  | 0.5 |  |  |  | 0.1 |  |
| Xylitol |  |  |  | 0.2 |  |  |  | 1 |  |  |  |
| Lactitol |  |  |  |  | 0.1 |  |  |  |  |  |  |
| Maltitol |  |  |  |  |  |  |  | 0.5 |  |  |  |
| Erythritol |  |  |  |  |  |  |  |  |  |  | 0.4 |
| Inositol |  |  |  |  |  |  | 0.3 |  |  |  |  |
| Threitol |  |  |  |  |  |  |  |  | 0.05 |  |  |
| Actipone Alpha-Pulp | 0.1 |  |  |  |  |  |  |  |  |  | 1 |
| Aqua, Butylene Glycol, Malic Acid, Actinidia Chinensis Fruit Extract, Citrus Aurantium Dulcis Juice, Citrus Paradisi Juice, Pyrus Malus Juice, Trideceth-9, Prunus Amydalus Dulcis Seed Extract |  |  |  |  |  |  |  |  |  |  |  |
| Allantoin | 0.1 |  |  |  |  |  |  |  |  |  |  |
| Allantoin |  |  |  |  |  |  |  |  |  |  |  |

TABLE 12-continued

Cosmetic formulations 1 to 11 (amounts in parts b.w.)

| Ingredients | 1 | 2 | 3 | 4 | 5 | 6 | 7 | 8 | 9 | 10 | 11 |
|---|---|---|---|---|---|---|---|---|---|---|---|
| Aloe Vera Gel Conc. 10:1 | | | | | | 0.2 | | | | | |
| Aloe Barbadensis(Aloe) Leaf Juice | | | | | | | | | | | |
| Aluminium Stearate | | | | 1.2 | | | | | | | |
| Aluminium Stearate | | | | | | | | | | | |
| Asebiol | | | | | | | | 3 | | | |
| Water, Pyridoxine HCL, Niacinamide, Glycerin, Panthenol, | | | | | | | | | | | |
| Hydrolyzed Yeast Protein, Threonine, Allantoin, Biotin | | | | | | | | | | | |
| Beta-Arbutin | | | | | | | | | 1 | | |
| Arbutin | | | | | | | | | | | |
| Arlypon ® F | | | | | | | 2 | | | | |
| Laureth-2 | | | | | | | | | | | |
| Asensa ® SC 220 | | | | | | | | | | | 2 |
| Polyethylene | | | | | | | | | | | |
| Azelaic acid | | | | | | | | | 0.5 | | |
| Azelaic acid | | | | | | | | | | | |
| Biotive L-Arginine | | 0.6 | | | | | | | | | |
| Arginine | | | | | | | | | | | |
| Biotive Troxerutin | | 0.5 | | | | | | | | | |
| Troxerutin | | | | | | | | | | | |
| (-)-alpha-Bisabolol | | | | | 0.1 | | | | | | |
| Bisabolol | | | | | | | | | | | |
| Carbopol Aqua SF-1 Polymer | | | | | | 5 | | | | | |
| Acrylates Copolymer | | | | | | | | | | | |
| Carbopol ® Ultrez-10 | | 0.2 | 0.2 | | | | | | | 0.2 | 0.3 |
| Carbomer | | | | | | | | | | | |
| Citric acid 10% in water | | | | | | 0.2 | 0.5 | | | | |
| Citric acid, water | | | | | | | | | | | |
| Colour | | | 0.04 | | | | | | | | |
| Crinipan ® AD | | | | | | | | 0.3 | | | |
| Climbazole | | | | | | | | | | | |
| Cutina ® AGS | | | | | | | | | | | 1.5 |
| Glycol Distearate | | | | | | | | | | | |
| Cutina ® PES | | | 2 | | | | | | | | |
| Pentaerythrityl Distearate | | | | | | | | | | | |
| D-Panthenol | | | | | | | | 0.5 | | | |
| Panthenol | | | | | | | | | | | |
| Dehyton K | | | | | | 8 | 8 | | | | |
| Cocamidopropyl Betaine | | | | | | | | | | | |
| Dow Corning 200(100 cs) | 2 | 2 | | | | | | | 0.5 | | |
| Silicone Fluid Dimethicone | | | | | | | | | | | |
| Dracorin ® CE | | | | 5 | | | | | | 2.5 | |
| Glyceryl Stearate Citrate | | | | | | | | | | | |
| Dracorin GOC | | | | | | | | 2.5 | | | |
| Glyceryl Oleate Citrate, Caprylic/Capric Triglyceride | | | | | | | | | | | |
| Dragocalm ® | 1 | | | | | | | | | | |
| Water (Aqua), Glycerin, Avena Sativa (Oat) Kernel Extract | | | | | | | | | | | |
| Dragoderm ® | | | | | | | | 0.5 | | | |
| Glycerin, Triticum Vulgare (Wheat) Gluten, Water (Aqua) | | | | | | | | | | | |
| Dragosan ® W/O P | | | | | 8 | | | | | | |
| Sorbitan Isostearate, Hydrogenated Castor Oil, Ceresin, | | | | | | | | | | | |
| Beeswax (Cera Alba) | | | | | | | | | | | |
| Dragosantol ® 100 | | | | | | 0.2 | | | | | |
| Bisabolol | | | | | | | | | | | |
| Dragosine ® | | 0.2 | 0.2 | | | | | | | | |
| Carnosine | | | | | | | | | | | |
| Dragoxat ® 89 | | | 5 | 7 | | | | 1 | | 5 | |
| Ethylhexyl Isononanoate | | | | | | | | | | | |
| Disodium EDTA | 0.1 | 0.1 | 0.1 | | | | | 0.1 | 0.1 | 0.05 | 0.05 |
| Disodium EDTA | | | | | | | | | | | |
| Emulsiphos ® | | | 2 | | | | | | 1.5 | | |
| Potassium Cetyl Phosphate, Hydrogenated Palm Glycerides | | | | | | | | | | | |
| Estearina L2SM GS | | | | | | | | | | | 2 |
| Stearic Acid, Palmitic Acid | | | | | | | | | | | |
| Ethanol | | | | | | | 2 | | | | |
| Ethanol | | | | | | | | | | | |
| Extrapone ® Aloe vera | | | | | 1 | | | | | | |
| Water (Aqua), Aloe Barbadensis, Propylene Glycol, Alcohol | | | | | | | | | | | |
| Extrapone Eucalyptus | | | | | | | | | | | 1 |
| Aqua, Propylene Glycol, Eucalyptus Globulus Leaf Extract | | | | | | | | | | | |
| Extrapone Iris B | | | | | | | 0.5 | | | | |
| Aqua, Propylene Glycol, PEG-40 Hydrogeanted Castor Oil, | | | | | | | | | | | |
| Tridecety-9, Bisabolol, Iris Germanica Root Extract | | | | | | | | | | | |
| Extrapone ® Witch Hazel | 1 | | | | | | | | | | |
| Propylene Glycol, Hamamelis Virginiana (Witch Hazel) Water, | | | | | | | | | | | |
| Water (Aqua), Hamamelis Virginiana (Witch Hazel) Extract | | | | | | | | | | | |

TABLE 12-continued

Cosmetic formulations 1 to 11 (amounts in parts b.w.)

| Ingredients | 1 | 2 | 3 | 4 | 5 | 6 | 7 | 8 | 9 | 10 | 11 |
|---|---|---|---|---|---|---|---|---|---|---|---|
| Food Color Brown E172 + E171 Powder<br>Titanium Dioxides (CI77891), Iron Oxides (CI77492), Iron Oxides (CI77491), Iron Oxides (CI77499) | | 2 | | | | | | 1.5 | | | |
| Food Color Titanium Dioxide Powder E171<br>Titanium Dioxides (CI77891) | | | | | | | | | | | 3 |
| Frescolat ® MGA<br>Menthone Glycerin Acetal | | | | | | | | | | | 0.5 |
| Frescolat ® ML<br>Menthyl Lactate | | | | | | 0.3 | 0.2 | | | 0.3 | |
| Frescolat Plus<br>Menthol, Menthyl Lactate | | | 0.2 | | | | | | | | |
| Frescolat ® X-Cool<br>Menthyl Ethylamido Oxalate | | | | | 0.2 | | | | | | |
| Genapol ® LRO Liquid<br>Sodium Laureth Sulfate | | | | | | | 37 | | | | |
| Glycerin<br>Glycerin | | | 3 | 3 | | | | 4.5 | 3 | 1.5 | 3 |
| Hydrolite ® 5<br>Pentylene Glycol | 3 | | | | 2 | | | | | | |
| Hydroviton-24 ®<br>Water (Aqua), Pentylene Glycol, Glycerin, Lactic Acid, Sodium Lactate, Serine, Urea, Sorbitol, Sodium Chloride, Allantoin | | | | 1 | | | | | | | |
| Hydroviton ® Plus 2290<br>Water (Aqua), Pentylene Glycol, Glycerin, Fructose, Urea, Citric acid, Sodium Hydroxide, Maltose, Sodium PCA, Sodium Chloride, Sodium Lactate, Trehalose, Allantoin, Sodium Hyaluronate, Glucose | | 2 | | | | | | | | | |
| Isoadipate<br>Diisopropyl Adipate | | | 2 | | | | | | 2 | | |
| Isodragol ®<br>Triisononanoin | 1 | | | | | | | | | | |
| Jojoba Oil<br>Simmondsia Chinensis (Jojoba) Seed Oil | | | | 0.3 | | | | | | | |
| Kaolin<br>Kaolin | | | | | | | | | | | 10 |
| Keltrol ® CG-RD<br>Xanthan Gum | | 0.2 | 0.1 | | | | | 0.3 | 0.2 | 0.3 | 1.2 |
| Kojic acid<br>Kojic Acid | | | | | | | | | 0.5 | | |
| KP-545<br>Cyclopentasiloxane Acrylates/Dimethicone Copolymer | | | | | | | | 1 | | | |
| Lanette ® 16<br>Cetyl Alcohol | | | | | | | | | 1.5 | 2 | |
| Lanette ® 22<br>Behenyl Alcohol | | | | | | | | | | | 3 |
| Lanette ® O<br>Cetearyl Alcohol | | | | 5 | | | | | | 2 | |
| Magnesium Sulfate<br>Magnesium Sulfate | | | | | 0.7 | | | | | | |
| Mineral Oil<br>Paraffinum Liquidum | | | | | 5 | | | | | | |
| Neo Heliopan ® 303<br>Octocrylene | | 4 | | | | | | 10 | | | |
| Neo Heliopan ® 357<br>Butylmethoxydibenzoyl-methane | | 2 | | | | | | 4 | 2 | | |
| Neo Heliopan ® AP 15% Lösung, neutralisiert mit L-Arginin Aqua, Disodium Phenyl Dibenzimidazole Tetrasulfonate, Arginin | | 6.7 | | | | | | | | | |
| Neo Heliopan ® AV<br>Ethylhexyl Methoxycinnamate | | | | | | | | | 7.5 | | |
| Neo Heliopan ® BB<br>Benzophenone-3 | | | | | | | | | 3 | | |
| Neo Heliopan ® E 1000<br>Isoamyl p.Methoxycinnamate | | 1 | | | | | | | | | |
| Neo Heliopan ® HMS<br>Homosalate | | | | | | | | 7 | 10 | | |
| Neo Heliopan ® OS<br>Ethylhexyl Salicylate | | 3 | | | | | | 5 | 5 | | |
| Neo Heliopan ® Hydro 20% Lösung, neutralisiert mit Biotive Arginine<br>Aqua, Phenylbenzimidazole, Sulphonic Acid, Arginin | | 10 | | | | | | 3.5 | | | |
| Neo-PCL Water Soluble N<br>Trideceth-9, PEG-5 Ethylhexanoate, Water (Aqua) | | | | | | | | 1.5 | | | 2 |
| Neutral oil<br>Caprylic/Capric Triglyceride | | | 2 | | | | | | | | |

TABLE 12-continued

Cosmetic formulations 1 to 11 (amounts in parts b.w.)

| Ingredients | 1 | 2 | 3 | 4 | 5 | 6 | 7 | 8 | 9 | 10 | 11 |
|---|---|---|---|---|---|---|---|---|---|---|---|
| Niacinamide | | | 2 | 0.5 | | 0.3 | | | | | |
| Niacinamide | | | | | | | | | | | |
| Ozokerite Wax 2389 | | | | 2 | | | | | | | |
| Ozokerite | | | | | | | | | | | |
| Parfume oil PFO1 or PFO2 | 0.05 | 0.3 | 1 | 0.3 | | 0.3 | 0.5 | | 0.3 | 0.1 | 0.5 |
| Parfum | | | | | | | | | | | |
| Passion Fruit Oil | | | 1 | | | | | | | | |
| Refined Passiflora Edulis seed oil | | | | | | | | | | | |
| PCL-Liquid 100 | 3 | 2 | | 5 | | | | | | | |
| Cetearyl Ethylhexanoate | | | | | | | | | | | |
| PCL-Solid | 1 | | | | | | | | | 2 | |
| Stearyl Heptanoate, Stearyl Caprylate | | | | | | | | | | | |
| Pemulen ® TR-2 | 0.6 | | | | | | | | 0.15 | | |
| Acrylates/C10-30 Alkyl Acrylate Crosspolymer | | | | | | | | | | | |
| Phenethyl Alcohol | | | | | 0.2 | | | | | | |
| Phenethyl Alcohol | | | | | | | | | | | |
| Phytoconcentrole ® | 1 | | | | | | | | | | |
| Shea Butter, Glycine Soja (Soybean) Oil, Butyrospermum Parkii (Shea Butter) | | | | | | | | | | | |
| Plantacare PS 10 | | | | | | | | | | | 5 |
| Sodium Laureth Sulfate, Lauryl Glucoside | | | | | | | | | | | |
| Polymer JR 400 | | | | | | | | 0.4 | | | |
| Sodium Laureth Sulfate, Lauryl Glucoside | | | | | | | | | | | |
| Retinol | | | | | 0.1 | | | | | | |
| Retinol | | | | | | | | | | | |
| Salicylic acid | | | | | | | | | | 0.5 | 0.3 |
| Salicylic Acid | | | | | | | | | | | |
| Sodium Ascorbyl Phosphate | | | | | | | | | 1 | | |
| Sodium Ascorbyl Phosphate | | | | | | | | | | | |
| Sodium Chloride | | | | | | | | 0.1 | | | |
| Sodium Chloride | | | | | | | | | | | |
| Sodium Hydroxide 10% Solution | 1 | | 0.5 | | 2 | | | | 0.2 | 1.9 | 1.1 |
| Sodium Hydroxide 10% Solution | | | | | | | | | | | |
| Softisan 100 | | | | 6 | | | | | | | |
| Hydrogenated Coco-Glycerides | | | | | | | | | | | |
| Solubilizer | | | | | | | 3 | | | | |
| PEG-40 Hydrogenated Castor Oil, Trideceth-9, Propylene Glycol, Water (Aqua) | | | | | | | | | | | |
| Sulfetal LA | | | | | 12 | | | | | | |
| Ammonium Lauryl Sulfate | | | | | | | | | | | |
| SymCalmin ® | 1 | | | | | | | 0.1 | | | 0.5 |
| Butylene Glycol, Pentylene Glycol, Hydroxyphenyl Propamidobenzoic Acid | | | | | | | | | | | |
| SymClariol ® | | | 0.1 | | 1 | | | | 0.2 | 0.38 | |
| Decylene Glycol | | | | | | | | | | | |
| SymDecanox HA | | | 1 | 2 | | | | | | | |
| Caprylic/Capric Triglyceride, Hydroxymethoxyphenyl Decanone | | | | | | | | | | | |
| Symdiol ® 68 | 1 | 0.5 | 0.5 | | | | | 0.5 | | 0.8 | |
| 1,2-Hexanediol, Caprylyl Glycol | | | | | | | | | | | |
| SymFinity ® 1298 | | | | 0.05 | | | | | | | |
| Echinacea Purpurea Extract | | | | | | | | | | | |
| SymGlucan ® | 1 | | | | | | | 2 | | | |
| Water (Aqua), Glycerin, Beta-Glucan | | | | | | | | | | | |
| SymHair ® Force 1631 | | | | | | | 2 | | | | |
| Pentylene Glycol, Isochrysis galbana Extract | | | | | | | | | | | |
| SymHelios ® 1031 | | 0.3 | | | | | | | | | |
| Benzylidene Dimethoxydimethylindanone | | | | | | | | | | | |
| SymLift | | 2 | | | | | | | | | |
| Water, Trehalose, Glycerin, Pentylene glycol, beta-Glucan, Hordeum Vulgare Seed Extract, Sodium Hyaluronate, 1,2-Hexanediol, Caprylyl glycol, Sodium Benzoate, Maltodextrin | | | | | | | | | | | |
| SymMatrix | | 0.2 | | | | | | | | | |
| Maltodextrin, Rubus Fruticosus (Blackberry) Leaf Extract | | | | | | | | | | | |
| SymMollient S | | | 1 | | | | | | | | |
| Cetearyl Nonanoate | | | | | | | | | | | |
| SymMollient ® W/S | | | 1 | | 2 | 1.5 | 2 | | | | |
| Trideceth-9, PEG-5 Isononanoate, Water (Aqua) | | | | | | | | | | | |
| SymOcide ® C | | | | | | | | 0.1 | | | |
| 0-Cymen-5-ol | | | | | | | | | | | |
| SymOcide ® PC | | | | | | | | | | 1 | |
| Phenoxyethanol, Caprylyl Glycol, | | | | | | | | | | | |
| SymOcide ® PH | | | | | | | 1 | | | | |
| Phenoxyethanol, Hydroxyacetophenone, Caprylyl Glycol, Water (Aqua) | | | | | | | | | | | |

TABLE 12-continued

Cosmetic formulations 1 to 11 (amounts in parts b.w.)

| Ingredients | 1 | 2 | 3 | 4 | 5 | 6 | 7 | 8 | 9 | 10 | 11 |
|---|---|---|---|---|---|---|---|---|---|---|---|
| SymOcide ® PS<br>Phenoxyethanol, Decylene Glycol, 1,2-Hexanediol | | | | | 0.8 | | | | | | 0.8 |
| SymOcide ® PT<br>Phenoxyethanol, Tropolone | | | | 0.8 | | | | | | | |
| SymPeptide ® 225<br>Glycerin, Water (Aqua), Myristoyl Pentapeptide-11 | | | | 1 | | | | | | | |
| SymRelief ® 100<br>Bisabolol, Zingiber Officinale (Ginger) Root Extract | | | | | | 0.1 | | | | | |
| SymRelief ® S<br>Bisabolol, Hydroxymethoxyphenyl Decanone | | | | | | | | | | 0.1 | |
| SymRepair ® 100<br>Hexyldecanol, Bisabolol, Cetylhydroxyproline Palmitamide,<br>Stearic Acid, Brassica Campestris (Rapeseed) Sterols | | 1 | | | | | | | | | |
| SymSave ® H<br>Hydoxyacetophenone | | 0.5 | 0.5 | | | 0.5 | | 0.5 | | | |
| SymSitive ® 1609<br>Pentylene Glycol, 4-t-Butylcyclohexanol | 1 | | | | | | | | 0.5 | | |
| SymVital ® AgeRepair 3040<br>Zingiber Officinale (Ginger) Root Extract | | 0.1 | | | | | | | | | |
| Sym White ® 377<br>Phenylethyl Resorcinol | | | | | | | | | 0.5 | | |
| Tetraselmis suecica extract 2.5% in glycerin/water<br>Water, Glycerin, Tetraselmis suecica extract | 1 | | | | | | | | | 2 | |
| Tetraselmis suecica extract spray-dried containing 95%<br>maltodextrin, 5% extract matter<br>Maltodextrin, Tetraselmis suecica extract | | | 0.25 | | | | | | | | |
| Vitacel CS 20 FC<br>Cellulose | | | | | | | | | 3 | | |
| Vitamin A Palmitate<br>Retinyl Palmitate | | | | 0.1 | | | | | | | |
| Vitamin E Acetate<br>Tocopheryl Acetate | | 0.5 | | 0.2 | | | | 0.5 | | 0.25 | |
| Willow bark extract<br>Salix Alba Extract | | | | | | | | | | | 0.1 |
| Xiameter PMX-345<br>Cyclopentasiloxane, Cyclohexasiloxane | | | | | | | | | | 6 | |
| Zetesol LA-2<br>Ammonium Laureth Sulfate | | | | | 26 | | | | | | |
| Water | | | | | Ad to 100 | | | | | | |

1 = Skin calming balm for sensitive oily skin
2 = Tinted Face Balm, SPF 15
3 = Rinse-off purifying mask for greasy skin
4 = Night cream W/O
5 = Facial Cleansing gel
6 = Face tonic for oily skin
7 = Anti-dandruff hair shampoo for greasy hair
8 = Sunscreen fluid for acne prone skin, SPF 30
9 = Skin lightening day care fluid O/W for impure oily skin
10 = Anti-acne skin cream
11 = 3 in 1 Skin purifying Wash + Scrub + Mask

TABLE 13

Cosmetic formulations 12 to 22 (amounts in parts b.w.)

| Ingredients | 12 | 13 | 14 | 15 | 16 | 17 | 18 | 19 | 20 | 21 | 22 |
|---|---|---|---|---|---|---|---|---|---|---|---|
| Mannitol | | 0.5 | | | | | 0.05 | | | | |
| Sorbitol | | | | | | | 0.3 | | | | |
| Xylitol | 0.3 | | | | | 0.5 | | | 0.2 | 0.1 | |
| Lactitol | | | | | 0.5 | | | | | | |
| Maltitol | | | | | | | | | | | |
| Erythritol | | | 0.1 | 0.2 | | | | | | | |
| Inositol | | | | | | | | | | | 0.4 |
| Threitol | | | | | | | | 0.1 | | | |
| Actipone ® White Tea GW<br>Aqua, Glycerin, Camellia Sinensis Leaf Extract | 1 | | | | | | | | | | |
| Actipone ® Witch Hazel<br>Hamamelis Virginiana Bark/Leaf/Twig Extract, Alcohol,<br>Hamamelis Virginiana Water | | | | | | | 3 | | 1 | | |
| Actipone ® Black Currant GW<br>Aqua, Glycerin, Ribes Nigrum Juice | | | | | 1 | | | | | | |
| Amisoft ® CS-11/CS-11(F) | | | | | 0.5 | | | | | | |

TABLE 13-continued

Cosmetic formulations 12 to 22 (amounts in parts b.w.)

| Ingredients | 12 | 13 | 14 | 15 | 16 | 17 | 18 | 19 | 20 | 21 | 22 |
|---|---|---|---|---|---|---|---|---|---|---|---|
| Sodium Cocoyl Glutamate | | | | | | | | | | | |
| Andiroba Oil, refined | | | | | | | | | | | 0.3 |
| Carapa Guaianensis Seed Oil | | | | | | | | | | | |
| Aristoflex ® AVC | | | | | | | | | 0.5 | | |
| Ammonium Acryloyoldimethyltaurate/VP Copolymer | | | | | | | | | | | |
| 5-Alpha-Avocuta | | | | | | | | 1 | | | |
| Butyl Avocadate | | | | | | | | | | | |
| Beeswax | | | | | | | | | 5 | | |
| Cera Alba | | | | | | | | | | | |
| Butylene Glycol | | 0.5 | | | | | 5 | | | | |
| Butylene Glycol | | | | | | | | | | | |
| Candelilla Wax | | | | | | | | | 15 | | |
| Euphorbia Cera (Candelilla) Wax | | | | | | | | | | | |
| Carnauba Wax | | | | | | | | | 5 | | |
| Cera Carnaubae depurata | | | | | | | | | | | |
| Carbopol ® Aqua SF-1 Polymer | | | | | 10 | | | | | | |
| Acrylates Copolymer | | | | | | | | | | | |
| CeramideBio | | | | | | | | | 0.5 | | |
| Cetylhydroxyproline Palmitamide | | | | | | | | | | | |
| Citric acid 10% in water | | | | 0.5 | | | | | 0.2 | | |
| Citric acid, water | | | | | | | | | | | |
| Crinipan ® AD | | | | | | | | | | 0.2 | |
| Climbazole | | | | | | | | | | | |
| Disodium EDTA | 0.1 | 0.05 | | | 0.1 | | | | | | 0.1 |
| Disodium EDTA | | | | | | | | | | | |
| Dow Corning 345 Fluid | | | | | | | | 5 | | | |
| Cyclomethicone | | | | | | | | | | | |
| Dow Corning 556 Fluid | | | | | | | | 4 | | | |
| Phenyl Trimethicone | | | | | | | | | | | |
| Dow Corning 2502 Fluid | | | | | | | | 5 | | | |
| Cetyl Dimethicone | | | | | | | | | | | |
| D-Panthenol 75 L | | | | | | | | | | 0.3 | |
| Panthenol | | | | | | | | | | | |
| Dracorin GOC | 2.5 | | | | | | | | | | |
| Glyceryl Oleate Citrate, Caprylic/Capric Triglyceride | | | | | | | | | | | |
| Dragoxat ® 89 | 5 | | | | 20 | | | | 2 | | |
| Ethylhexyl Isononanoate | | | | | | | | | | | |
| Emulsiphos ® | | | | | | | | | 2 | | |
| Potassium Cetyl Phosphate, Hydrogenated Palm Glycerides | | | | | | | | | | | |
| Ethanol | | | | | | 5 | 5 | | 10 | | |
| Alcohol, Aqua | | | | | | | | | | | |
| Evermat | | | 3 | | | | | | | | |
| Enantia chlorantha bark extract | | | | | | | | | | | |
| Extrapone ® Strawberry B | | | | | | 1 | | | | | |
| Aqua, Propylene Glycol, Citric Acid, Trideceth-9, Bisabolol, Fragaria Ananassa Fruit Extract | | | | | | | | | | | |
| Extrapone ® Tiger Grass | | | | | | | 5 | | 1 | | |
| Aqua, Glycerin, PEG-40 Hydrogenated Castor Oil, Trideceth-9, Centella Asiatica Extract | | | | | | | | | | | |
| Flowerconcentrole ® | | | | | | | | | 2 | | |
| Frangipani Pentylene Glycol, Bisabolol, Plumeria Acutifolia Flower Extract L | | | | | | | | | | | |
| Frescolat ® ML | | | | | 0.3 | 0.3 | 0.3 | | 0.5 | | |
| Menthyl Lactate | | | | | | | | | | | |
| Glycerin | 3 | 3 | 3 | | | 5 | | | | | 1 |
| Glycerin | | | | | | | | | | | |
| Green Pigment | | | | | | | | 0.85 | | | |
| CI77288, Triethoxycaprylylsilane | | | | | | | | | | | |
| Hexylene Glycol | | | | 25 | | | | | | | |
| Hexylene Glycol | | | | | | | | | | | |
| Hispagel ® 200 | | | | | | 1 | 1 | | | | |
| Glycerin, Glyceryl Polyacrylate | | | | | | | | | | | |
| Hydrolite ® 5 | 1.5 | | | 3 | 1 | 4 | 5 | | 7 | | |
| Pentylene Glycol | | | | | | | | | | | |
| Hydrolite ® 6 | | | | | 0.5 | | | | | | |
| 1,2-Hexanediol | | | | | | | | | | | |
| Hydromoist ® L | | | | | | | | | | | 1 |
| Aqua, Hydrolyzed Lupine Seed Extract | | | | | | | | | | | |
| Hydroviton ® Plus 2290 | | | | 1 | | 1 | | | | | |
| Water (Aqua), Pentylene Glycol, Glycerin, Fructose, Urea, Citric acid, Sodium Hydroxide, Maltose, Sodium PCA, Sodium Chloride, Sodium Lactate, Trehalose, Allantoin, Sodium Hyaluronate, Glucose | | | | | | | | | | | |
| Icroquat Behenyl TMS-50 | | | | | | | | | | | 2 |
| Behentrimonium Methosulfate, Cetyl Alcohol, Butylene Glycol | | | | | | | | | | | |

TABLE 13-continued

Cosmetic formulations 12 to 22 (amounts in parts b.w.)

| Ingredients | 12 | 13 | 14 | 15 | 16 | 17 | 18 | 19 | 20 | 21 | 22 |
|---|---|---|---|---|---|---|---|---|---|---|---|
| Isoadipate | | | | | | | | 12.7 | | | |
| Diisopropyl Adipate | | | | | | | | | | | |
| Isodragol ® | | | | | | | | 8 | | | |
| Triisononanoin | | | | | | | | | | | |
| Isopropyl Myristate | | | | | | | | | | | 2 |
| Isopropyl Myristate | | | | | | | | | | | |
| Jaguar ® Excel | | | | | | | | | 0.1 | | |
| Guar Hydroxypropyltrimonium Chloride | | | | | | | | | | | |
| Jojoba Oil | | | | | | | | 8 | | | 0.5 |
| Simmondsia Chinensis (Jojoba) Seed Oil | | | | | | | | | | | |
| Keltrol ® CG-T | | | | | | 0.1 | 0.2 | | | 0.3 | |
| Xanthan Gum | | | | | | | | | | | |
| Lactic acid | | | | 0.2 | | | | | | | |
| Lactic acid | | | | | | | | | | | |
| Lanette ® 16 | 1 | 1 | | | | | | | | | 3 |
| Cetyl Alcohol | | | | | | | | | | | |
| Lanette ® 18 | | | | | | | | | 4 | | |
| Stearyl Alcohol | | | | | | | | | | | |
| Lanette ® 22 | | | | | | | | | 2 | | |
| Behenyl Alcohol | | | | | | | | | | | |
| Lanette ® O | | | | | | | | | 1 | | 4.5 |
| Cetearyl Alcohol | | | | | | | | | | | |
| Medialan ® LD | | | | 10 | | | | | | | |
| Sodium Lauroyl Sarcosinate | | | | | | | | | | | |
| Mineral Oil | | | | | | | | | | | 1 |
| Paraffinum Liquidum | | | | | | | | | | | |
| Miniporyl ® | 1 | | | | | | | | | | |
| Isopentyldiol, Trifolium Pratense (Clover) Flower Extract | | | | | | | | | | | |
| Neo-PCL Water Soluble N | | | | | | | 1.5 | | | | |
| Trideceth-9, PEG-5 Ethylhexanoate, Aqua | | | | | | | | | | | |
| Niacinamide | | 0.5 | 0.3 | | | | | | 0.5 | | 0.4 |
| Niacinamide | | | | | | | | | | | |
| Parfume oil PFO1 or PFO2 | 0.5 | | 0.3 | 1 | | 0.5 | | 0.3 | | 0.1 | 0.5 |
| Parfum | | | | | | | | | | | |
| PCL-Liquid 100 | | | | 5 | | | | | 2 | | |
| Cetearyl Ethylhexanoate | | | | | | | | | | | |
| PCL-Solid | | | | | | | | 3 | | | |
| Stearyl Heptanoate, Stearyl Caprylate | | | | | | | | | | | |
| Pemulen TR-2 Polymeric Emusifier | 0.3 | | | | | | | | | | |
| Acrylates/C10-30 Alkyl Acrylate Crosspolymer | | | | | | | | | | | |
| Plantacare ® 2000 UP | | | 15 | | | | | | | | |
| Decyl Glucoside | | | | | | | | | | | |
| Potassium Sorbate | | | | 0.2 | | | | | | | |
| Potassium sorbate | | | | | | | | | | | |
| Propylene Glycol | | 2 | | | | | | | | 5 | |
| Propylene Glycol | | | | | | | | | | | |
| Retinopeptide 189 | 1 | | | | | | | | | | |
| Glycerin, Pentylene Glycol, Aqua, Myristoyl Nonapeptide-3 | | | | | | | | | | | |
| Salicylic Acid | 0.3 | | | | | 0.1 | 0.3 | 0.2 | | | |
| Salicylic Acid | | | | | | | | | | | |
| Shea Butter (Organic) | | | | | | | | 20 | | | |
| Butyrospermum Parkii (Shea) Butter | | | | | | | | | | | |
| Sodium Benzoate | | | | 0.2 | | | | | | | |
| Sodium Benzoate | | | | | | | | | | | |
| Sodium Chloride | | | | 6 | | | | | | | |
| Sodium Chloride | | | | | | | | | | | |
| Sodium Hydroxide 10% solution | 2.43 | | | | 2 | 0.58 | 0.46 | | | | |
| Sodium Hydroxide, water | | | | | | | | | | | |
| Softigen ® 767 | | | 3 | | | | | | | | |
| PEG-6, Caprylic/Capric Glycerides | | | | | | | | | | | |
| Solubilizer | | | | | | | | 1.2 | | 2 | |
| PEG-40 Hydrogenated Castor Oil, Trideceth-9, Propylene Glycol, Water (Aqua) | | | | | | | | | | | |
| SymCalmin ® | | | | | | | | | | 0.5 | |
| Butylene Glycol, Pentylene Glycol, Hydroxyphenyl Propamidobenzoic Acid | | | | | | | | | | | |
| SymClariol ® | | 0.3 | 0.5 | | | | | 0.3 | | | |
| Decylene Glycol | | | | | | | | | | | |
| SymDecanox HA | | | | | | | | 2 | | | 0.5 |
| Caprylic/Capric Triglyceride, Hydroxymethoxyphenyl Decanone | | | | | | | | | | | |
| Symdiol ® 68 | | 0.5 | 0.8 | | | | 0.5 | | 0.5 | 0.5 | |
| 1,2-Hexanediol, Caprylyl Glycol | | | | | | | | | | | |
| SymHair ® Restore | | | | | | | | | | 0.5 | 1 |
| Glycerin, Triticum Vulgare Protein, Aqua | | | | | | | | | | | |
| SymHair ® Shield | | | | | | | | | | | 0.5 |

TABLE 13-continued

Cosmetic formulations 12 to 22 (amounts in parts b.w.)

| Ingredients | 12 | 13 | 14 | 15 | 16 | 17 | 18 | 19 | 20 | 21 | 22 |
|---|---|---|---|---|---|---|---|---|---|---|---|
| Pentylene Glycol, Aqua, Glycerin, Triticum Vulgare Bran Extract, 1,2-Hexanediol, Caprylyl Glycol | | | | | | | | | | | |
| SymMatrix | | | | | | | 0.3 | | | | |
| Maltodextrin, Rubus Fruticosus (Blackberry) Leaf Extract | | | | | | | | | | | |
| SymMollient ® S | | | | | | | | | 2 | | 2 |
| Cetearyl Nonanoate | | | | | | | | | | | |
| SymMollient ® W/S | | 2 | 1.5 | | | 2 | | | 3 | | |
| Trideceth-9, PEG-5 Isononanoate, Water (Aqua) | | | | | | | | | | | |
| SymOcide ® PS | | | | | | 1 | | | | | 0.8 |
| Phenoxyethanol, Decylene Glycol, 1,2-Hexanediol | | | | | | | | | | | |
| SymRelief ® S | | | | | | | | 0.1 | | | |
| Bisabolol, Hydroxymethoxyphenyl Decanone | | | | | | | | | | | |
| SymSave ® H | 0.5 | 0.5 | | | 0.5 | | | | 0.5 | | |
| Hydoxyacetophenone | | | | | | | | | | | |
| SymSitive ® 1609 | | | | | 1 | | | | | | |
| Pentylene Glycol, 4-t-Butylcyclohexanol | | | | | | | | | | | |
| SymSol ® PF-3 | | 1.5 | | | 3 | 1.2 | | | | | |
| Aqua, Pentylene Glycol, Sodium Lauryl Sulfoacetate, Sodium Oleoyl Sarcosinate, Sodium Chloride, Sodium Oleate | | | | | | | | | | | |
| SymVital ® AgeRepair 3040 | | | | | 0.2 | | | | | | |
| Zingiber Officinale (Ginger) Root Extract | | | | | | | | | | | |
| Tetraselmis suecica extract 2.5% in glycerin/water | | | | | | | | | 1 | | |
| Water, Glycerin, Tetraselmis suecica extract | | | | | | | | | | | |
| Tetraselmis suecica extract spray-dried containing 95% maltodextrin, 5% extract matter | | | | 0.25 | | | | | | | |
| Maltodextrin, Tetraselmis suecica extract | | | | | | | | | | | |
| White Pigment | | | | | | | | 7 | | | |
| CI77891, Ricinus (Castor) Seed oil | | | | | | | | | | | |
| Witch Hazel-Distillate | | | | | | | | | | 1 | |
| Hamamelis Virginiana (Witch Hazel) Water, Water (Aqua), Alcohol | | | | | | | | | | | |
| Xiameter ® PMX-200 Silicone Fluid 100 cs | 1 | | | | | | | | 0.5 | | |
| Dimethicone | | | | | | | | | | | |
| Xiameter ® XM OFX-0193 Fluid | | | | | | 1 | 1 | | | | |
| PEG-12 Dimethicone | | | | | | | | | | | |
| Yellow Pigment | | | | | | | | 0.15 | | | |
| CI77492, Triethoxycaprylylsilane | | | | | | | | | | | |
| Water | | | | | | Ad 100 | | | | | |
| Aqua | | | | | | | | | | | |

12 = Pore Refining Fluid
13 = Make-Up Remover Wipes Solution for impure skin
14 = Anti-acne Cleansing Mousse
15 = 3-Phases Clear Make-up Remover Lotion for oily skin
16 = Eau micellaire
17 = Purifying/Anti-Imperfections Cocktail
18 = Tightening Serum for young skin
19 = Concealer Stick
20 = Hair Mask
21 = Aqueous-based Hair & Scalp Serum
22 = Hair Conditioner

The invention claimed is:

1. A composition comprising: a sugar alcohol and a *Tetraselmis* extract, wherein the total sugar alcohol content is in an amount of ≥16 wt. % in the overall composition, calculated based on the extract dry weight, and wherein the *Tetraselmis* extract comprises the following based on the extract dry weight:
   a) total minerals ≥10 wt. % of the total *Tetraselmis* extract composition, and
   b) total galactose ≥3 wt. % of the total *Tetraselmis* extract composition, and
   c) total glucose ≥2 wt. % of the total *Tetraselmis* extract composition, and
   d) total amino acids ≥3 wt. % of the total *Tetraselmis* extract composition, and
   e) total nitrogen ≥2 wt. % of the total *Tetraselmis* extract composition;
   wherein the extract is obtained by extracting cells of *Tetraselmis suecica* using a liquid extractant at a temperature higher than 60° C.

2. A composition according to claim 1, wherein the sugar alcohol is selected from one or more of: C4, C5, C6, C7 sugar alcohols and disaccharide sugar alcohols.

3. A composition according to claim 1, wherein the sugar alcohol is selected from one or more of: threitol (C4 sugar alcohol), erythritol (C4 sugar alcohol), ribitol (C5 sugar alcohol), arabitol (C5 sugar alcohol), xylitol (C5 sugar alcohol), sorbitol (C6 sugar alcohol), mannitol (C6 sugar alcohol), dulcitol (galactitol) (C6 sugar alcohol), inositol (cyclic C6 sugar alcohol), volemitol (C7 sugar alcohol), lactitol D-galactopyranolsyl-D-glucitol; disaccharide sugar alcohol), maltitol (4-O-α-glucopyranosyl-D-sorbitol; disaccharide sugar alcohol) and their respective enantiomers.

4. A composition according to claim 1 further comprising niacinamide.

5. A composition according to claim 4, wherein the weight ratio range of sugar alcohol and *Tetraselmis* extract together in relation to niacinamide is 1:10000 to 1:1, calculated based on the extract dry weight.

6. A cosmetic composition comprising a composition according to claim 1, the cosmetic composition further optionally comprising auxiliary substances and/or perfumes, wherein the cosmetic composition is a skin and/or hair care product.

7. A dermatological or therapeutic product comprising a composition according to claim 1, wherein the amount of the composition according to claim 1 in the product is 0.001 to 10 wt. % in the total dermatological or therapeutic product.

8. A cosmetic composition according to claim 6, wherein the amount of the composition according to claim 1, is 0.0001 to 10 wt. % in the total cosmetic composition or cosmetic product.

9. A pharmaceutical or cosmetic composition comprising the composition according to claim 1,
wherein the sugar alcohol is mannitol,
wherein the *Tetraselmis suecica* extract comprises the following based on the extract dry weight:
a) total minerals ≥10 wt. % of the total *Tetraselmis suecica* extract composition, and
b) total galactose ≥3 wt. % of the total *Tetraselmis suecica* extract composition, and
c) total glucose ≥4 wt. % of the total *Tetraselmis suecica* extract composition, and
d) total amino acids ≥3 wt. % of the total *Tetraselmis suecica* extract composition, and
e) total nitrogen ≥2 wt. % of the total *Tetraselmis suecica* extract composition;
wherein the *Tetraselmis suecica* extract is obtained by extracting cells of *Tetraselmis suecica* with a liquid extractant at a temperature higher than or equal to 75° C.;
wherein the *Tetraselmis* extract has a total Arginine content, which is the sum of free and bound Arginine, of between 0.6 to 1.0 wt. % of the total composition, based on the extract dry weight; and
wherein the ratio of the total sugar alcohol content to the sugar alcohol content in the *Tetraselmis suecica* extract based on the extract dry weight is ≥1.1:1.

* * * * *